US009538941B2

(12) United States Patent
Perez et al.

(10) Patent No.: US 9,538,941 B2
(45) Date of Patent: Jan. 10, 2017

(54) DEVICES AND METHODS FOR EXPRESSION OF BODILY FLUIDS FROM AN INCISION

(75) Inventors: Edward Perez, Menlo Park, CA (US); Charles C. Raney, Scotts Valley, CA (US); Paul Patel, Sunnyvale, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1233 days.

(21) Appl. No.: 12/797,854

(22) Filed: Jun. 10, 2010

(65) Prior Publication Data

US 2010/0249653 A1 Sep. 30, 2010

Related U.S. Application Data

(60) Division of application No. 12/353,666, filed on Jan. 14, 2009, now Pat. No. 7,758,518, which is a
(Continued)

(51) Int. Cl.
| | | |
|---|---|---|
| *A61B 5/145* | (2006.01) | |
| *A61B 5/15* | (2006.01) | |
| *A61B 5/151* | (2006.01) | |

(52) U.S. Cl.
CPC ......... *A61B 5/14514* (2013.01); *A61B 5/1519* (2013.01); *A61B 5/150022* (2013.01);
(Continued)

(58) Field of Classification Search
CPC ............. A61B 5/14514; A61B 5/15113; A61B 5/150022; A61B 5/150503; A61B 5/15194; A61B 5/150412; A61B 5/150068; A61B 5/15128; A61B 5/1519; A61B 5/150213; A61B 5/150358; A61B 5/15117; A61B 5/14532
(Continued)

(56) References Cited

U.S. PATENT DOCUMENTS

| 1,960,889 A | 5/1934 | Benedict |
| 2,594,621 A | 4/1952 | Derrick |
| (Continued) | | |

FOREIGN PATENT DOCUMENTS

| DE | 34 26 090 | 4/1985 |
| DE | 37 08 031 | 11/1987 |
| (Continued) | | |

OTHER PUBLICATIONS

"A Subcutaneous Capillary Filtrate Collector for Measurement of Blood Chemistries", Ash et al., ASAIO Journal, pp. M416-M420, issue/vol. 38 (3), J.B. Lippincott Co., 1992.
(Continued)

*Primary Examiner* — Rene Towa
(74) *Attorney, Agent, or Firm* — Woodard, Emhardt, Moriarty, McNett & Henry LLP

(57) ABSTRACT

Systems and methods for the expression of bodily fluid from an incision in the skin include devices which bear against the skin in a manner to retain the fluid adjacent the incision site and urge the fluid inwardly toward the incision. Systems utilize a constricting member, a bi-stable expression member, or a pressing member. The present invention further encompasses combinations of the foregoing expression systems with each other, as well as with other expression devices known in the art. Moreover, the invention includes the combination of the expression systems with incising, sampling and/or testing systems, particularly in a single, integrated device. The present invention also contemplates the associated methods for expressing bodily fluid from an incision, including in combination with methods for incising, sampling and/or testing of the bodily fluid.

18 Claims, 13 Drawing Sheets

Related U.S. Application Data continuation of application No. 10/165,102, filed on Jun. 7, 2002, now abandoned, which is a continuation-in-part of application No. 09/879,991, filed on Jun. 14, 2001, now Pat. No. 6,706,000.

(60) Provisional application No. 60/296,949, filed on Jun. 8, 2001, provisional application No. 60/296,950, filed on Jun. 8, 2001, provisional application No. 60/315,873, filed on Aug. 29, 2001, provisional application No. 60/315,968, filed on Aug. 29, 2001.

(52) U.S. Cl.
CPC .... *A61B 5/150068* (2013.01); *A61B 5/15113* (2013.01); *A61B 5/15117* (2013.01); *A61B 5/15128* (2013.01); *A61B 5/15194* (2013.01); *A61B 5/150213* (2013.01); *A61B 5/150358* (2013.01); *A61B 5/150412* (2013.01); *A61B 5/150503* (2013.01); *A61B 5/14532* (2013.01)

(58) Field of Classification Search
USPC . 600/573, 576, 578, 580, 583; 606/181–182
See application file for complete search history.

(56) References Cited

U.S. PATENT DOCUMENTS

| | | |
|---|---|---|
| 2,646,799 A | 7/1953 | Jacoby, Jr. |
| 2,660,169 A | 11/1953 | Malm |
| 2,660,369 A * | 11/1953 | Malm .................. 235/60.39 |
| 2,714,890 A | 8/1955 | Vang |
| 3,030,959 A | 4/1962 | Grunert |
| 3,040,744 A | 6/1962 | Hoggard |
| 3,068,868 A | 12/1962 | Skopyk |
| 3,208,452 A | 9/1965 | Stern |
| 3,221,739 A | 12/1965 | Rosenthal |
| 3,235,337 A | 2/1966 | Artis |
| 3,358,689 A | 12/1967 | Higgins |
| 3,486,504 A | 12/1969 | Austin |
| 3,623,475 A | 11/1971 | Sanz |
| 3,626,929 A | 12/1971 | Sanz et al. |
| 3,673,475 A | 6/1972 | Britton, Jr. |
| 3,685,509 A | 8/1972 | Bentall |
| 3,734,085 A | 5/1973 | Russell |
| 3,741,197 A | 6/1973 | Sanz et al. |
| 3,774,611 A | 11/1973 | Tussey et al. |
| 3,933,439 A | 1/1976 | McDonald |
| D238,710 S | 2/1976 | Cacanindin |
| 3,964,482 A | 6/1976 | Gerstel et al. |
| 4,151,832 A | 5/1979 | Hamer |
| 4,154,228 A | 5/1979 | Feldstein et al. |
| D254,444 S | 3/1980 | Levine |
| 4,203,446 A | 5/1980 | Hofert et al. |
| 4,218,421 A | 8/1980 | Mack, Jr. et al. |
| 4,222,380 A | 9/1980 | Terayama |
| 4,235,234 A | 11/1980 | Whitney et al. |
| 4,356,826 A | 11/1982 | Kubota |
| 4,360,016 A | 11/1982 | Sarrine |
| 4,368,738 A | 1/1983 | Tersteegen et al. |
| 4,375,815 A | 3/1983 | Burns |
| 4,383,530 A | 5/1983 | Bruno |
| 4,397,643 A | 8/1983 | Rygiel |
| 4,441,510 A | 4/1984 | Worley et al. |
| 4,449,529 A | 5/1984 | Burns et al. |
| 4,460,354 A | 7/1984 | Weilbacher et al. |
| 4,462,405 A | 7/1984 | Ehrlich |
| 4,469,110 A | 9/1984 | Slama |
| 4,503,856 A | 3/1985 | Cornell et al. |
| 4,517,978 A | 5/1985 | Levin et al. |
| 4,531,943 A | 7/1985 | Van Tassel et al. |
| 4,564,513 A | 1/1986 | Becher et al. |
| 4,577,630 A | 3/1986 | Nitzsche et al. |
| 4,580,564 A | 4/1986 | Anderson |
| 4,622,974 A | 11/1986 | Coleman et al. |
| 4,637,403 A | 1/1987 | Garcia et al. |
| 4,637,978 A | 1/1987 | Dappen |
| 4,648,408 A | 3/1987 | Hutcheson et al. |
| 4,653,511 A | 3/1987 | Goch |
| 4,653,513 A | 3/1987 | Dombrowski |
| 4,658,821 A | 4/1987 | Chiodo et al. |
| 4,660,570 A | 4/1987 | Dombrowski |
| 4,677,979 A | 7/1987 | Burns |
| 4,685,463 A | 8/1987 | Williams |
| 4,687,000 A | 8/1987 | Eisenhardt et al. |
| 4,735,203 A | 4/1988 | Ryder et al. |
| 4,750,489 A | 6/1988 | Berkman et al. |
| 4,787,398 A | 11/1988 | Garcia et al. |
| 4,790,979 A | 12/1988 | Terminiello et al. |
| 4,794,926 A | 1/1989 | Munsch et al. |
| 4,805,623 A | 2/1989 | Jobsis |
| RE32,922 E | 5/1989 | Levin et al. |
| 4,844,095 A | 7/1989 | Chiodo et al. |
| 4,850,973 A | 7/1989 | Jordan et al. |
| 4,858,607 A | 8/1989 | Jordan et al. |
| 4,869,249 A | 9/1989 | Crossman et al. |
| 4,873,993 A | 10/1989 | Meserol et al. |
| 4,883,068 A | 11/1989 | Dechow |
| D305,065 S | 12/1989 | Büchel et al. |
| 4,895,147 A | 1/1990 | Bodicky et al. |
| 4,920,977 A | 5/1990 | Haynes |
| 4,924,879 A | 5/1990 | O'Brien |
| 4,925,447 A | 5/1990 | Rosenblatt |
| 4,953,552 A | 9/1990 | DeMarzo |
| 4,976,724 A | 12/1990 | Nieto et al. |
| 4,981,473 A | 1/1991 | Rosenblatt |
| 4,990,154 A | 2/1991 | Brown et al. |
| 4,994,068 A | 2/1991 | Hufnagle |
| 4,994,073 A | 2/1991 | Green |
| 4,994,079 A | 2/1991 | Genese et al. |
| 4,995,402 A | 2/1991 | Smith et al. |
| 5,002,054 A | 3/1991 | Ash et al. |
| 5,014,718 A | 5/1991 | Mitchen |
| 5,019,059 A | 5/1991 | Goldberg et al. |
| 5,029,583 A | 7/1991 | Meserol et al. |
| 5,035,704 A | 7/1991 | Lambert et al. |
| 5,052,403 A | 10/1991 | Haber et al. |
| 5,054,499 A | 10/1991 | Swierczek |
| 5,066,859 A | 11/1991 | Karkar et al. |
| 5,070,884 A | 12/1991 | Columbus et al. |
| 5,070,886 A | 12/1991 | Mitchen et al. |
| D324,423 S | 3/1992 | Ahlstrand et al. |
| 5,097,810 A | 3/1992 | Fishman et al. |
| 5,102,404 A | 4/1992 | Goldberg et al. |
| 5,145,565 A | 9/1992 | Kater et al. |
| 5,163,442 A | 11/1992 | Ono |
| 5,165,418 A | 11/1992 | Tankovich |
| D332,306 S | 1/1993 | Garth et al. |
| 5,188,118 A | 2/1993 | Terwilliger |
| 5,189,751 A | 3/1993 | Giuliani et al. |
| 5,193,552 A | 3/1993 | Columbus et al. |
| 5,195,534 A | 3/1993 | Sarrine |
| 5,201,324 A | 4/1993 | Swierczek |
| 5,217,480 A | 6/1993 | Haber et al. |
| 5,222,504 A | 6/1993 | Solomon |
| 5,228,972 A | 7/1993 | Osaka et al. |
| 5,231,993 A | 8/1993 | Haber et al. |
| 5,271,385 A | 12/1993 | Bailey |
| 5,277,198 A | 1/1994 | Kanner et al. |
| 5,279,294 A | 1/1994 | Anderson et al. |
| 5,279,586 A | 1/1994 | Balkwill |
| 5,282,822 A | 2/1994 | Macors et al. |
| 5,304,193 A | 4/1994 | Zhadanov |
| 5,309,924 A | 5/1994 | Peabody |
| 5,318,583 A | 6/1994 | Rabenau et al. |
| 5,318,584 A | 6/1994 | Lange et al. |
| 5,320,607 A | 6/1994 | Ishibashi |
| 5,320,808 A | 6/1994 | Holen et al. |
| 5,322,609 A | 6/1994 | Graham |
| 5,324,302 A | 6/1994 | Crouse |
| 5,324,303 A | 6/1994 | Strong et al. |
| 5,353,806 A | 10/1994 | Heinzelman et al. |
| 5,366,470 A | 11/1994 | Ramel |
| 5,368,047 A | 11/1994 | Suzuki et al. |

(56) References Cited

U.S. PATENT DOCUMENTS

| | | |
|---|---|---|
| 5,387,203 A | 2/1995 | Goodrich |
| 5,395,387 A | 3/1995 | Burns |
| 5,402,798 A | 4/1995 | Swierczek et al. |
| 5,421,816 A | 6/1995 | Lipkovker |
| 5,423,758 A | 6/1995 | Shaw |
| 5,423,847 A | 6/1995 | Strong et al. |
| 5,445,611 A | 8/1995 | Eppstein et al. |
| 5,456,875 A | 10/1995 | Lambert |
| 5,458,140 A | 10/1995 | Eppstein et al. |
| 5,472,427 A | 12/1995 | Rammler |
| 5,474,084 A | 12/1995 | Cunniff |
| 5,487,748 A | 1/1996 | Marshall et al. |
| 5,512,158 A | 4/1996 | Cole |
| 5,518,006 A | 5/1996 | Mawhirt et al. |
| 5,529,074 A | 6/1996 | Greenfield |
| D371,440 S | 7/1996 | Petersen |
| 5,540,709 A | 7/1996 | Ramel |
| 5,545,173 A | 8/1996 | Herbst |
| 5,545,174 A | 8/1996 | Schenk et al. |
| 5,549,584 A | 8/1996 | Gross |
| 5,554,166 A | 9/1996 | Lange et al. |
| 5,569,212 A | 10/1996 | Brown |
| 5,575,403 A | 11/1996 | Charlton et al. |
| 5,582,184 A | 12/1996 | Erickson et al. |
| D378,612 S | 3/1997 | Clark et al. |
| 5,607,401 A | 3/1997 | Humphrey |
| 5,611,809 A | 3/1997 | Marshall et al. |
| 5,613,978 A | 3/1997 | Harding |
| 5,624,458 A | 4/1997 | Lipscher |
| 5,628,309 A | 5/1997 | Brown |
| 5,628,764 A | 5/1997 | Schraga |
| 5,628,765 A | 5/1997 | Morita |
| 5,630,986 A | 5/1997 | Charlton et al. |
| 5,632,410 A | 5/1997 | Moulton et al. |
| 5,638,828 A | 6/1997 | Lauks et al. |
| 5,662,127 A | 9/1997 | De Vaughn |
| 5,666,966 A | 9/1997 | Horie et al. |
| 5,671,753 A | 9/1997 | Pitesky |
| 5,680,872 A | 10/1997 | Sesekura et al. |
| 5,682,233 A | 10/1997 | Brinda |
| 5,700,695 A | 12/1997 | Yassinzadeh et al. |
| 5,707,384 A | 1/1998 | Kim |
| 5,709,699 A | 1/1998 | Warner |
| 5,714,390 A | 2/1998 | Hallowitz et al. |
| 5,720,924 A | 2/1998 | Eikmeier et al. |
| 5,730,357 A | 3/1998 | Besenschek et al. |
| 5,730,753 A | 3/1998 | Morita |
| 5,738,244 A | 4/1998 | Charlton et al. |
| 5,741,291 A | 4/1998 | Yoo |
| RE35,803 E | 5/1998 | Lange et al. |
| 5,746,217 A | 5/1998 | Erickson et al. |
| 5,755,733 A | 5/1998 | Morita |
| 5,788,652 A | 8/1998 | Rahn |
| 5,800,781 A | 9/1998 | Gavin et al. |
| 5,820,570 A | 10/1998 | Erickson et al. |
| 5,823,973 A | 10/1998 | Racchini et al. |
| 5,830,219 A | 11/1998 | Bird et al. |
| 5,846,490 A | 12/1998 | Yokota et al. |
| 5,851,215 A | 12/1998 | Mawhirt et al. |
| 5,854,074 A | 12/1998 | Charlton et al. |
| 5,855,801 A | 1/1999 | Lin et al. |
| 5,857,983 A | 1/1999 | Douglas et al. |
| 5,863,800 A | 1/1999 | Eikmeier et al. |
| 5,871,494 A | 2/1999 | Simons et al. |
| 5,872,713 A * | 2/1999 | Douglas et al. ............... 702/85 |
| 5,873,887 A | 2/1999 | King et al. |
| 5,879,311 A | 3/1999 | Duchon et al. |
| 5,882,317 A | 3/1999 | Saito et al. |
| 5,885,211 A | 3/1999 | Eppstein et al. |
| 5,885,219 A | 3/1999 | Nightengale |
| 5,891,053 A | 4/1999 | Sesekura |
| 5,902,279 A | 5/1999 | Powles et al. |
| 5,916,222 A | 6/1999 | Iwasaki et al. |
| 5,916,229 A | 6/1999 | Evans |
| 5,916,230 A | 6/1999 | Brenneman et al. |
| 5,947,957 A | 9/1999 | Morris |
| 5,951,492 A | 9/1999 | Douglas et al. |
| 5,951,493 A * | 9/1999 | Douglas et al. ............... 600/583 |
| 5,951,582 A | 9/1999 | Thorne et al. |
| 5,964,718 A | 10/1999 | Duchon et al. |
| 5,968,063 A | 10/1999 | Chu et al. |
| 5,971,941 A | 10/1999 | Simons et al. |
| 5,984,940 A | 11/1999 | Davis et al. |
| 5,997,561 A | 12/1999 | Bocker et al. |
| 6,015,392 A | 1/2000 | Douglas et al. |
| 6,022,366 A | 2/2000 | Schraga |
| 6,027,459 A | 2/2000 | Shain et al. |
| 6,036,924 A | 3/2000 | Simons et al. |
| 6,045,567 A | 4/2000 | Taylor et al. |
| 6,048,352 A | 4/2000 | Douglas et al. |
| 6,056,701 A | 5/2000 | Duchon et al. |
| 6,056,765 A * | 5/2000 | Bajaj et al. ................... 606/181 |
| 6,063,039 A | 5/2000 | Cunningham et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,294 A | 6/2000 | Simons et al. |
| 6,080,116 A | 6/2000 | Erickson et al. |
| 6,086,545 A | 7/2000 | Roe et al. |
| 6,093,156 A | 7/2000 | Cunningham et al. |
| 6,099,484 A | 8/2000 | Douglas et al. |
| 6,120,462 A | 9/2000 | Hibner et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A | 11/2000 | Heller et al. |
| 6,152,889 A | 11/2000 | Sopp et al. |
| 6,152,942 A | 11/2000 | Brenneman et al. |
| 6,155,992 A | 12/2000 | Henning et al. |
| 6,156,050 A | 12/2000 | Davis et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,434 B1 | 2/2001 | Eppstein |
| 6,183,489 B1 | 2/2001 | Douglas et al. |
| 6,193,673 B1 | 2/2001 | Viola et al. |
| 6,203,504 B1 | 3/2001 | Latterell et al. |
| 6,210,420 B1 | 4/2001 | Mauze et al. |
| 6,210,421 B1 | 4/2001 | Bocker et al. |
| 6,231,531 B1 | 5/2001 | Lum et al. |
| 6,261,241 B1 | 7/2001 | Burbank et al. |
| 6,261,244 B1 | 7/2001 | Kensey et al. |
| 6,261,245 B1 | 7/2001 | Kawai et al. |
| 6,283,926 B1 | 9/2001 | Cunningham et al. |
| 6,283,982 B1 | 9/2001 | Levaughn et al. |
| 6,285,454 B1 | 9/2001 | Douglas et al. |
| 6,306,104 B1 * | 10/2001 | Cunningham et al. ....... 600/573 |
| 6,306,152 B1 | 10/2001 | Verdonk et al. |
| 6,315,738 B1 * | 11/2001 | Nishikawa et al. ........... 600/583 |
| 6,319,210 B1 | 11/2001 | Douglas et al. |
| 6,332,871 B1 | 12/2001 | Douglas et al. |
| 6,346,114 B1 | 2/2002 | Schraga |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,419,661 B1 | 7/2002 | Kuhr et al. |
| 6,423,011 B1 | 7/2002 | Arulkumaran et al. |
| 6,461,496 B1 | 10/2002 | Feldman et al. |
| 6,464,649 B1 | 10/2002 | Duchon et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |

(56) References Cited

U.S. PATENT DOCUMENTS

| | | |
|---|---|---|
| 6,571,651 B1 | 6/2003 | Hodges |
| 6,589,260 B1 | 7/2003 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,730,046 B1 | 5/2004 | Hamamoto et al. |
| 6,743,211 B1 * | 6/2004 | Prausnitz et al. ............. 604/239 |
| 6,752,817 B2 | 6/2004 | Flora et al. |
| 7,041,068 B2 | 5/2006 | Freeman et al. |
| 7,879,211 B2 * | 2/2011 | Katsuki et al. .......... 204/403.01 |
| 2001/0011157 A1 | 8/2001 | Latterell et al. |
| 2001/0027327 A1 | 10/2001 | Schraga |
| 2001/0031931 A1 | 10/2001 | Cunningham et al. |
| 2001/0039387 A1 | 11/2001 | Rutynowski et al. |
| 2001/0044615 A1 | 11/2001 | Amano et al. |
| 2002/0002344 A1 | 1/2002 | Douglas et al. |
| 2002/0004196 A1 | 1/2002 | Whitson |
| 2002/0022789 A1 | 2/2002 | Perez et al. |
| 2002/0029059 A1 | 3/2002 | Purcell |
| 2002/0040230 A1 | 4/2002 | Kuhr et al. |
| 2002/0052618 A1 | 5/2002 | Haar et al. |
| 2002/0077584 A1 | 6/2002 | Lin et al. |
| 2002/0082522 A1 | 6/2002 | Douglas et al. |
| 2002/0082543 A1 | 6/2002 | Park et al. |
| 2002/0103499 A1 | 8/2002 | Perez et al. |
| 2002/0115967 A1 | 8/2002 | Svedman |
| 2002/0169470 A1 | 11/2002 | Kuhr et al. |
| 2002/0177761 A1 | 11/2002 | Orloff et al. |
| 2002/0177788 A1 | 11/2002 | Hodges et al. |
| 2003/0199902 A1 | 10/2003 | Boecker et al. |

FOREIGN PATENT DOCUMENTS

| | | |
|---|---|---|
| DE | 42 34 553 A1 | 4/1993 |
| DE | 198 19 407 A1 | 11/1999 |
| EP | 0 212 906 | 4/1987 |
| EP | 0 453 283 | 10/1991 |
| EP | 0 622 046 A2 | 2/1994 |
| EP | 0 671 146 A1 | 9/1995 |
| EP | 0 688 532 A2 | 12/1995 |
| JP | H09-084781 | 9/1995 |
| JP | 8000598 | 1/1996 |
| JP | H11-164825 | 6/1999 |
| JP | 2000-116768 | 4/2000 |
| WO | WO 85/04089 A1 | 9/1985 |
| WO | WO 93/09723 | 5/1993 |
| WO | WO 95/10223 | 4/1995 |
| WO | WO 96/33403 | 10/1996 |
| WO | WO 96/37256 A1 | 11/1996 |
| WO | WO 97/08986 | 3/1997 |
| WO | WO 97/42882 | 11/1997 |
| WO | WO 97/42885 | 11/1997 |
| WO | WO 97/42886 | 11/1997 |
| WO | WO 97/43962 A1 | 11/1997 |
| WO | WO 99/26539 | 10/1999 |
| WO | WO 99/55232 | 11/1999 |
| WO | WO 01/64105 | 9/2001 |
| WO | WO 01/73395 | 10/2001 |
| WO | WO 01/89383 | 11/2001 |

OTHER PUBLICATIONS

"Diabetes Mellitus: Biosensors for Research and Management", Turner et al., Biosensors, pp. 85-115, issue/vol. 1 (1)), Elsevier Applied Science Publishers, 1985.

"Interstitium & Lymphatic Techniques", Korthuis, R.J. et al., Microcirculatory Technology, pp. 317-340, Academic Press, Inc., 1986.

"Microlet Choice", Instructions on How to Use the Microlet Choice Low Pressure Sampling Blood Instrument, Japanese language document and English translation, Jun. 1997.

"Re-evaluation of the Needle Method for Measuring Interstitial Fluid Pressure", Brace et al., American journal of Physiology, pp. 603-607, issue/vol. 229 (3), American Physiological Society, 1975.

"Suction Effusion Fluid from Skin and Constituent Analysis: New Candidate for Interstitial Fluid", Kayashima et al., American Journal of Physiology, pp. H1623-H1627, issue/vol. 263 (5), American Physiological Society, 1992.

"Use of a Capillary Filtrate Collector for Monitoring Glucose in Diabetics", Janie-Swain et al., ASAIO Journal, pp. 336-340, J.B. Lippincott Co., 1987.

"A Subcutaneous Capillary Filtrate Collector for Measurement of Blood Chemistries", Ash et al., ASAIO Journal, pp. M699-M705, issue/vol. 39 (3), J.B. Lippincott Co., 1993.

"An Overview of Minimally Invasive Technologie", Ginsberg, Clinical Chemistry, pp. 1596-1600, issue/vol. 38 (9), Becton Dickinson and Co., 1992.

\* cited by examiner

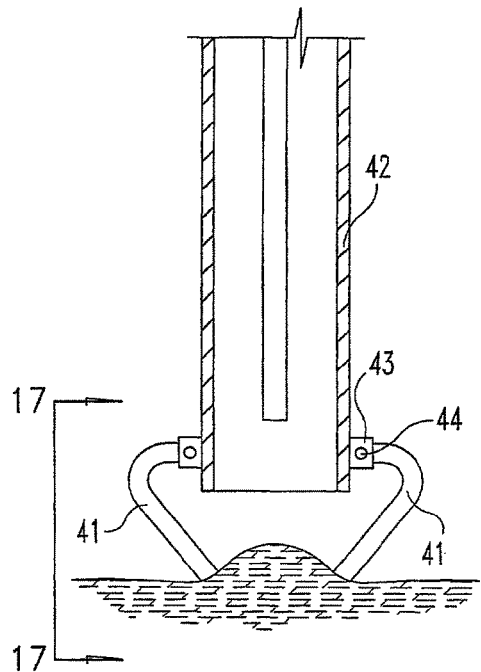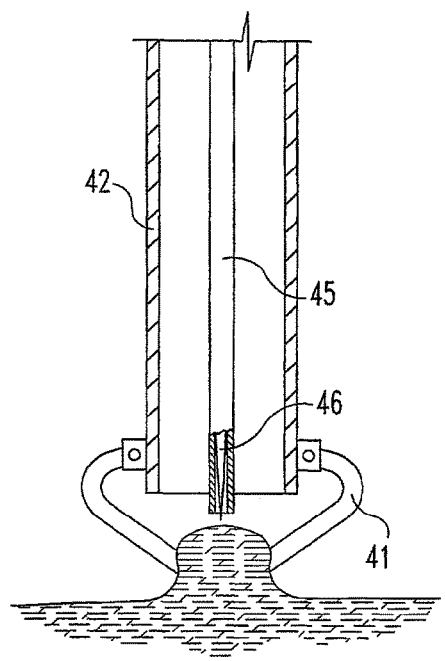
*Fig. 15*        *Fig. 16*
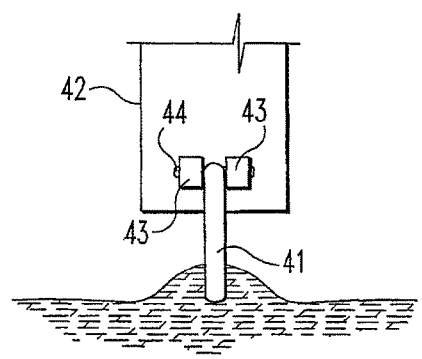
*Fig. 17*

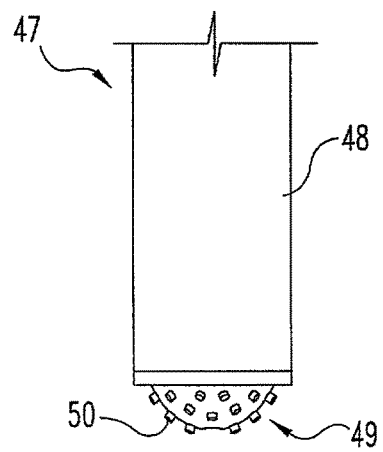
Fig. 18
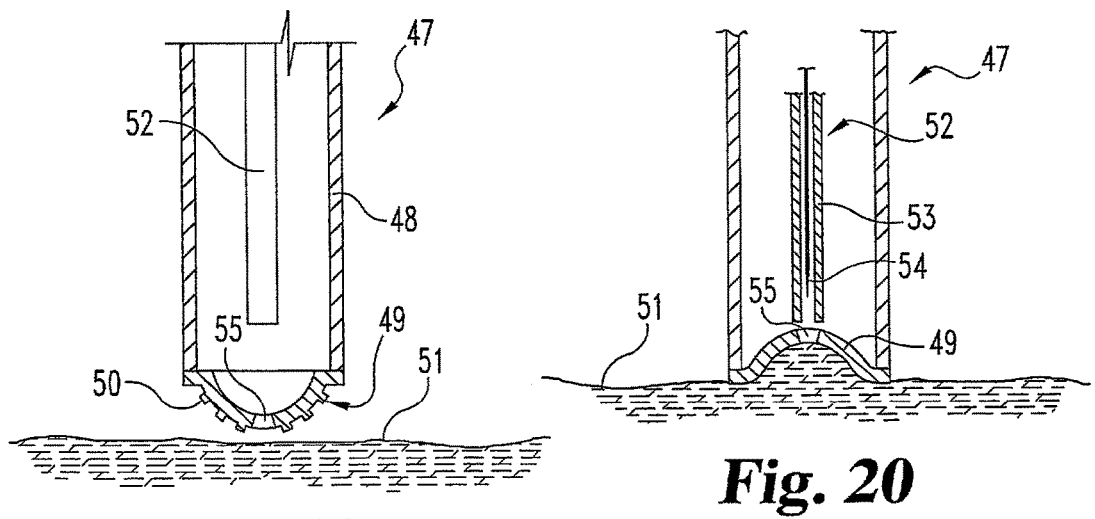
Fig. 19
Fig. 20

DEVICES AND METHODS FOR EXPRESSION OF BODILY FLUIDS FROM AN INCISION

CROSS-REFERENCE TO RELATED APPLICATIONS

This application is a divisional of U.S. application Ser. No. 12/353,666, filed Jan. 14, 2009, now issued as U.S. Pat. No. 7,758,518, which is a continuation of U.S. application Ser. No. 10/165,102, filed Jun. 7, 2002, now abandoned, which is a continuation-in-part of U.S. patent application Ser. No. 09/879,991, filed Jun. 14, 2001, now U.S. Pat. No. 6,706,000, and U.S. application Ser. No. 10/165,102 claims the benefit of U.S. Patent Provisional Application No. 60/296,949, filed Jun. 8, 2001, U.S. Provisional Application No. 60/296,950, filed Jun. 8, 2001, U.S. Provisional Patent Application No. 60/315,873, filed Aug. 29, 2001, and U.S. Provisional Application No. 60/315,968, filed Aug. 29, 2001. The entireties of the aforementioned applications are hereby incorporated by reference.

FIELD OF THE INVENTION

The present invention relates to the sampling of a bodily fluid obtained from an incision in the skin, and more particularly to acquiring the fluid by capillary action. The invention also may include the combination of such sampling devices and methods with incising, expressing, and/or testing systems.

BACKGROUND OF THE INVENTION

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

The testing of bodily fluids basically involves the steps of obtaining the fluid sample, transferring the sample to a test device, conducting a test on the fluid sample, and displaying the results. These steps are generally performed by a plurality of separate instruments or devices.

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re 35,803, issued to Lange, et al. on May 19, 1998; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; 6,099,484, issued to Douglas et al. on Aug. 8, 2000; and 6,332,871, issued to Douglas et al. on Dec. 25, 2001. Examples of commercial sampling devices include the Roche Compact, Amira AtLast, Glucometer Elite and Therasense FreeStyle test strips.

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

The present invention provides for enhancing the fluid sampling and testing by assisting in the expression of the fluid from the incision. Expression of the fluid is always useful in order to increase the quantity of bodily fluid available for acquisition by a sampling device. Such larger quantities make it easier to quickly and reliably acquire the fluid, and reduce the potential that there will be an insufficient quantity of fluid acquired for testing to be performed. When used at the fingertip, expression results in an even larger quantity of fluid being produced in a shorter period of time, thereby providing a suitable amount of fluid for tests requiring relatively larger quantities. When used at alternate sites, the fluid expression can be important to provide a sufficient quantity of fluid to be acquired and tested by a given system.

SUMMARY OF THE INVENTION

The present invention provides various systems and methods for the expression of bodily fluid from an incision in the skin. The invention encompasses separate expression devices as well as combination systems including incising, sampling and/or testing systems.

Systems and methods for the expression of bodily fluid from an incision in the skin include devices which bear against the skin in a manner to retain the fluid adjacent the incision site and urge the fluid inwardly toward the incision. One system utilizes a constricting member which engages the skin at initial, outer positions, and moves to draw the skin into an inner position forming a bulged, pinch of skin containing the incision site. The constricting member comprises flexible or non-flexible components, and is formed as a single, continuous member or as a plurality of discrete elements. A second system includes a bi-stable expression member including a skin-engaging portion having a first, outwardly bulged condition, and a second, inverted condition the skin is drawn into and retained within the member. The exterior surface of the expression member is optionally configured or treated to enhance the grasping of the skin. A third system involves a pressing member including deformable portions defining opposed, skin-engaging surfaces which are displaced upon pressing the member against the skin a sufficient amount. The deformable portions comprise flexible or non-flexible components, and are formed as a single, continuous member or as a plurality of discrete elements. The present invention further encompasses the combination of the foregoing expression systems with each other, as well as with other expression devices known in the art. Moreover, the invention includes the combination of the expression systems with incising, sampling and/or testing systems, particularly in a single, integrated device. The present invention also contemplates the associated methods for expressing bodily fluid from an incision, including in combination with methods for incising, sampling and/or testing of the bodily fluid.

In accordance with one aspect of the present invention, there is provided a device for expressing bodily fluid from an incision site which includes a body and a constricting member connected to the body and defining opposed, skin-engaging surfaces. The constricting member has a first condition with the skin-engaging surfaces contacting the skin at initial, outer positions, and a second condition with the skin-engaging surfaces engaging and drawing the skin into an inner position forming a bulged, pinch of skin containing the incision site. The constricting member deforms or moves between the first and second conditions, and may comprise flexible or non-flexible components. The constricting member may also be formed as a single, continuous member or as a plurality of discrete elements.

In accordance with a second aspect of the present invention, there is provided a device for expressing bodily fluid from an incision site including a body defining a cavity and a bi-stable expression member connected to the body adjacent to the interior cavity. The expression member includes a skin-engaging portion having first and second stable conditions, with the portion in the first stable condition being outwardly bulged relative to the body, and the portion in the second stable condition being inverted and received within the cavity of the body. The exterior of the skin-engaging portion includes an exterior surface and defines an aperture communicating between the exterior surface and the cavity. The skin-engaging portion engages the skin and draws the skin into the member as the skin-engaging portion inverts from the first condition to the second condition. The exterior surface of the skin-engaging portion is optionally configured or treated to enhance the grasping of the skin, such as by providing projections or a sticky coating.

In a third aspect, the present invention provides a device for expressing bodily fluid from an incision site which includes a body and a pressing member connected with the body and including deformable portions defining opposed, skin-engaging surfaces. The deformable portions having first positions contacting the skin and second positions engaging the skin and displaced from the first positions. The deformable portions are configured to deform from the first positions to the second positions upon pressing the member against the skin a sufficient amount. The deformable portions of the pressing member may comprise flexible or non-flexible components, and may also be formed as a single, continuous member or as a plurality of discrete elements.

The present invention further encompasses the combination of the foregoing expression systems with each other, as well as with other expression devices known in the art. Moreover, the invention includes the combination of the expression systems with incising, sampling and/or testing systems, particularly in a single, integrated device. The present invention also contemplates the associated methods for expressing bodily fluid from an incision, including in combination with methods for incising, sampling and/or testing of the bodily fluid.

BRIEF DESCRIPTION OF THE DRAWINGS

FIG. 15 is a side, elevational view, partially in cross-section, showing a further embodiment of the present invention including movable, rigid constricting elements.

FIG. 16 is a side, elevational view, partially in cross-section, showing the device of FIG. 15 with the elements in the constricting position.

FIG. 17 is a partial, side view of the device of FIG. 15, showing the attachment of the constricting elements.

FIG. 18 is a side, elevational view of another embodiment of an expression system in accordance with the present invention.

FIG. 19 is a side, cross-sectional view of the device of FIG. 18.

FIG. 20 is a side, cross-sectional view of the device of FIG. 18, showing the expression member in the inverted position.

DETAILED DESCRIPTION OF THE ILLUSTRATED EMBODIMENTS

Figure 1:
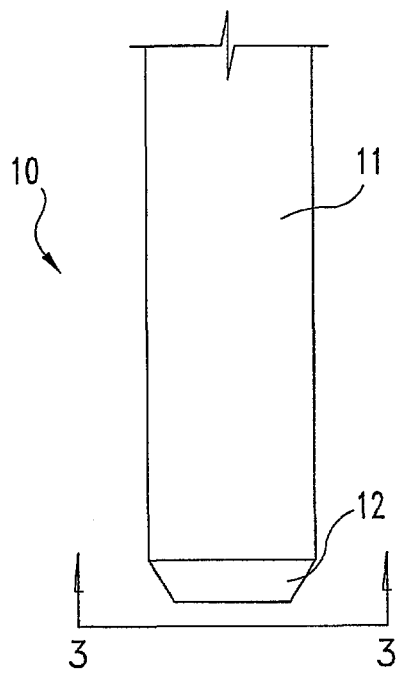
FIG. 1 is a front, elevational view of a fluid testing device including an expression system in accordance with an embodiment of the present invention.
Figure 2:
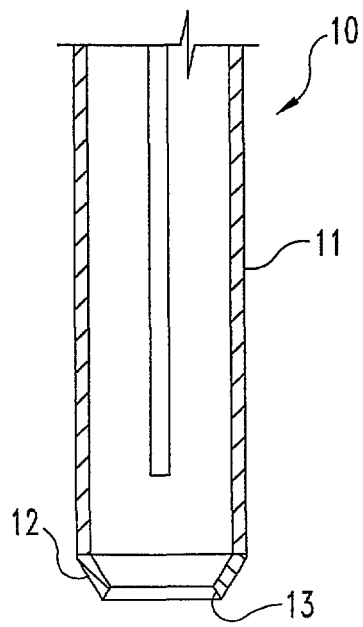
FIG. 2 is a cross-sectional view of the testing device of FIG. 1.
Figure 3:
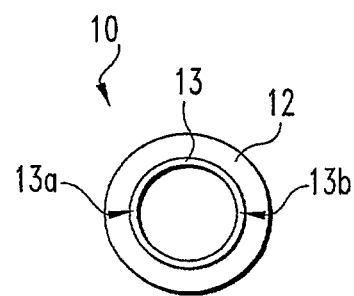
FIG. 3 is a distal end, plan view of the testing device of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and methods, and such further applications of the principles of the invention as illustrated therein being contemplated as would normally occur to one skilled in the art to which the invention relates.

The present invention provides a variety of devices and methods which separately or in combination are useful in enhancing the expression of fluid from an incision in the skin. This expression of the fluid results in a fluid sample that is larger, and/or produced more quickly, than would otherwise result. Expression of a bodily fluid from an incision is desirable in many instances. The lancing of the skin may produce a sufficient quantity of blood or interstitial fluid, but expression of the fluid from the incision will provide greater assurance that a sufficient quantity has been produced, and that the sample may be successfully and readily acquired. Also, expression of the bodily fluid is advantageous in the use of alternate test sites, such as the palm or forearm, because the quantity of fluid produced without expression can be significantly less than the amount produced at the fingertip. While some test devices will operate with greatly reduced fluid volumes, a greater volume of fluid makes it easier to acquire the fluid for testing. The present invention provides devices and methods that greatly enhance the expression of fluid from an incision.

The expression of fluid is also important when used in combination devices. The expression of fluid in the context of an integrated lancing and sampling device, for example, is advantageous since it is more difficult to view the fluid sample and it is therefore more important that the sample is sufficient for sampling and testing purposes. The present invention is readily combined in a single, integrated unit with incising, sampling and/or testing devices.

The fluid is obtained from an incision formed in the surface of the skin. The incising of the skin may be accomplished by any suitable means, including cutting with a mechanical instrument, laser, high speed fluid stream, etc. Of these, lancing the skin is most common and is preferred, and specific descriptions herein use lancing for purposes of example. It will be appreciated, however, that lancing is only exemplary, and all forms of making an incision in the skin are included.

The depth of penetration generally controls the fluid produced, particularly in combination with the characteristics of the incision site. The present invention is useful with various bodily fluids, including blood or interstitial fluid. The incising device may be configured for production of either blood or interstitial fluid, for example, by controlling the distance which the incising device extends into the user's skin. For example, a depth of 0.25 mm to 4 mm will typically produce blood from the dermis, while a depth of 0.05 mm to 0.5 mm will produce interstitial fluid from the epidermis.

The present invention encompasses the concept that bodily fluid can be expressed from an incision by a variety of methods and devices that retain the fluid adjacent the incision and/or urge the fluid toward the incision. One concept involves constricting the area surrounding the incision, thereby retaining the bodily fluid within the constricted location and at the same time urging the fluid toward the incision. A second concept involves pressing the skin surrounding the incision, thereby increasing the pressure on the fluid and forcing it to move toward and out of the incision. A third concept involves the "kneading" of the skin by moving a device along the skin in the direction of the incision, thereby pushing the fluid toward and out of the incision. The present invention further contemplates the combination of any two or all three of these modes of expression.

The fluid expression functions to facilitate the production of fluid at the site of an incision. As used herein, the term "incision" is intended to cover any opening in the skin that permits direct access to the bodily fluid. Unless indicated otherwise, the expression systems can be used before and/or after the incision is formed. Therefore the term "incision site" is intended to include the site where an incision either has been or will be formed, unless from the context or express language it is clear otherwise.

One of the approaches to expression in accordance with the present invention is the constriction of the skin surrounding the site of the incision. The constriction may occur before, during and/or after the incision is formed. The term constriction is intended herein to refer to contacting the skin at locations outward of the incision site and then moving a portion of the skin inward toward the incision site and holding the skin in that position. The initial engagement of the skin and the subsequent movement inwardly of the skin essentially grasps the skin at the surface and pinches the skin in a manner to retain it in the constricted position. This provides a portion of skin around the incision site that is engaged by the constriction device and is retained in this position for a period of time, typically while the incising and sampling take place. The skin will have the appearance of a raised pucker or pinch of skin which includes the incision site. This constriction of the skin is distinguished from mere pressing against the skin. The bodily fluid is held within the region of the constriction and is also urged toward the incision by pressure generated by the constricting device.

In one embodiment, the constriction device comprises a deformable member positioned at the end of a support housing. The deformable member engages the skin as the device is initially pressed against the skin. As the device is further pressed against the skin, the member deforms such that the engaging surface grasps the skin and moves it inwardly toward the incision site. In this embodiment, the deformed member is preferably configured such that pressing the member against the skin automatically causes the member to deform in a manner that constricts the skin. In a preferred embodiment, the deformation of the member comprises non-permanent flexing of the member between the outer and inner positions. However, the invention also contemplates the use of a member that deforms in a manner that is permanent, or at least not fully reversible. The deforming member may be constructed from a variety of pliable, biocompatible materials suitable to produce such flexing or other deformation, including for example silicone, urethane, polyvinyl chloride, delrin, and various other natural and synthetic materials having the requisite physical properties.

Referring in particular to the drawings, there is shown a fluid expression device 10 constructed in accordance with a first embodiment of the present invention. Device 10 (FIG. 1) includes a housing 11 having a deformable expression member 12 at the end thereof. For purposes of illustration, the deformable member is described hereafter with respect to a flexible member. Housing 11 is typically an elongated, cylindrical member which is readily grasped by the user, but the housing may have a variety of other shapes. The material used for the housing is not critical, and may comprise, for example, various metals and plastics. The housing typically will contain other systems for incising, sampling and/or testing the bodily fluid.

Figure 4:
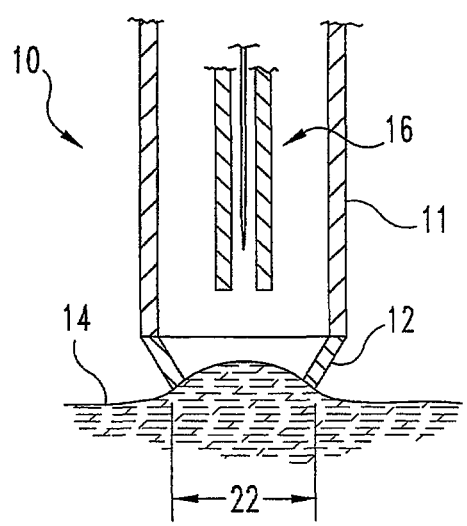
FIG. 4 is a partial, cross-sectional view of the testing device of FIG. 1.
Figure 5:
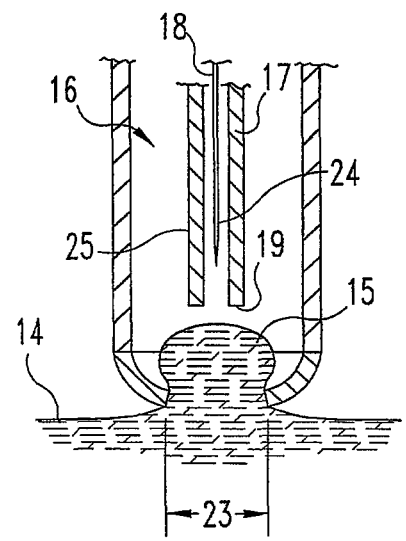
FIG. 5 is a partial cross-sectional view of the device, showing the expression member in the constricting position.

The expression member 12 is connected to or integral with the housing and defines a plurality of distal end, skin-engaging surfaces, for example, 13a and 13b. In the embodiment shown, the expression member comprises a continuous, perimetric surface 13 defining the opposed, skin-engaging surfaces. The surfaces are "opposed" in the sense that movement of the surfaces will result in the constriction of the skin as previously described. The surfaces move from a first, skin-contacting position (FIG. 4) to a second, skin-constricting position (FIG. 5). The surfaces may move directly toward each other, or simply in a direction sufficient to constrict the skin. For example, one set of skin-engaging surfaces could move in parallel toward a second set of opposed, skin-engaging surfaces. Also, one or more of the skin-engaging surfaces may be fixed relative to the housing, while other of the surfaces move relative to the fixed surfaces. In a preferred embodiment, the skin-engaging member provides surfaces which fall within a circular pattern and the surfaces are then preferably diametrically opposed, or equi-radially spaced about the circular configuration. In deforming, the circular or other form of the member may reduce in size or may change shape. In the latter instance, for example, a circular shape may be changed to an oval or oblong shape such that the skin is pinched from two opposing sides.

In use, the surfaces 13 contact the skin surface 14 as the device 10 is pressed (downwardly in FIG. 4) against the skin. The device is then pressed further against the skin and the surfaces 13 engage the skin and urge the skin inward as the expression member flexes (FIG. 5). This action produces an upwardly-bulged, pinch of skin 15. The inward and upward movements of the skin-engaging surfaces constrict the skin, holding bodily fluid within the constricted area and applying a pressure that will urge the fluid toward and out of an incision.

The expression member 12 has been described as being a flexible member. This indicates that releasing the pressure and removing the device from the skin will result in a return of the member to the starting shape shown in FIG. 4. The use of a flexible member is preferable in that the device is thereby available for repeated use. However, alternatively the deformation of the member may be permanent or only partially reversible. In that event, the member will not return to its original shape. Such devices may not be reusable without replacement of the deforming expression member. However, this may be suitable in certain applications, such as in a clinical setting where it would be appropriate to replace the skin-engaging member after each use. The deforming member can be readily adapted for replacement on the housing, such as by the use of a snap, press or threaded fit of the member to the housing.

The constriction device finds particular advantage in combination with an incising system constituting a part of an overall integrated device. As used herein, incising is intended to mean generally any way to form an incision in the skin to enable fluid to be accessed directly. Described hereafter is an exemplary device using a lancet to form the incision.

Figure 6:
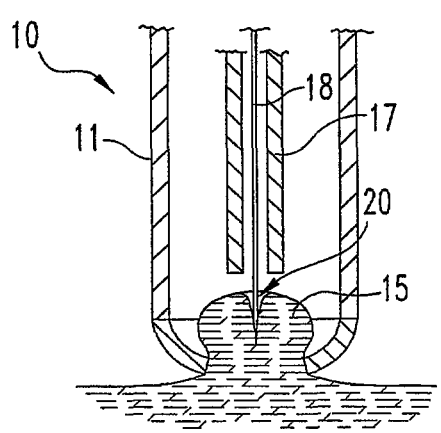
FIG. 6 is a partial cross-sectional view of the device, showing the incising of the skin.

As shown in the drawings, the device 10 may include, for example, a lancing device 16 operable to incise the bulged skin. In this version, the lancing device 16 includes a capillary tube 17 and a lancet 18 longitudinally movable within the capillary tube. In accordance with the method depicted in the drawings, the lancing device 16 is positioned to have its distal end adjacent the pinch of skin formed by the constriction device (FIG. 5). The lancet 18 is then advanced beyond the end 19 of the capillary tube 17 a predetermined distance to enter the skin and form an incision 20 of desired depth (FIG. 6). The lancet 18 is then withdrawn from the incision and a drop of blood or interstitial fluid 21 exits from the incision.

The constriction of the skin adjacent the incision ensures that fluid within that region will be retained, rather than moving away from the site. The constriction of the skin further provides a bulged, pressurized pinch of skin 15 which tends to spread the incision apart after it is formed. This facilitates the expression of fluid from the incision since the skin is prevented from reclosing around the incision. In addition, the pressure maintained by the constricting member urges fluid to exit the incision once it is formed.

The spacing and movement of the skin-engaging surfaces of the constriction member are selected to provide the desired expression results. The member 13 moves between a first condition with the surfaces contacting the skin and located at initial, outer positions (FIG. 4), and a second condition with the surfaces engaging the skin and located at constricting, inner positions (FIG. 5). The skin is drawn inward as the skin-engaging surfaces move from the outer positions to the inner positions. The initial and constricted spacings of the skin-engaging surfaces may be varied depending on the targeted bodily fluid, the incision site, for example, the finger versus alternate sites, and other considerations. In a typical device, for example, the outer contacting dimension 22 (FIG. 4) is about 5 to about 30 mm, preferably about 15 to about 25 mm, and the inner constricting dimension 23 (FIG. 5) is about 2 to about 9 mm, preferably about 6 to about 8 mm.

The particular procedure represented in the drawings involves the constricting of the skin prior to and during lancing. It will be appreciated, however, that the constriction may also be applied simultaneously with or after the formation of the incision. Further, the constriction device is shown as being combined in a single device with the lancing system. However, the constricting device is also applicable for use as a separate device that is applied to the skin over an incision site.

Figure 7:
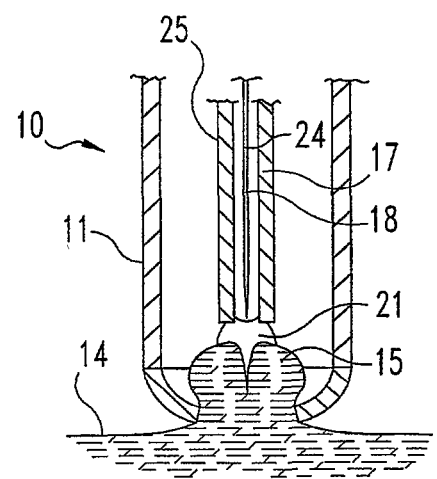
FIG. 7 is a partial cross-sectional view of the device showing the acquisition of the bodily fluid by a sampling system.

The described embodiment further demonstrates the inclusion of a sampling device useful for acquiring the fluid formed at the incision site. The capillary tube 17 defines an annular, capillary passageway 24 between the lancet 18 and the interior wall of the capillary tube. The capillary tube is positioned to contact the fluid droplet 21 as it forms (FIG. 7). As the droplet is generated, it eventually grows to a sufficient size that it contacts the end opening of the capillary passageway. The fluid is then drawn upwardly into the annular passageway 24 by capillary action. This action can be enhanced by using a capillary tube having an interior passageway which is formed of a material that is naturally hydrophilic or has been treated to be hydrophilic, or which is covered, e.g., coated, with a hydrophilic material. The capillary tube may further be treated or constructed to have a hydrophobic outer surface 25 to inhibit attraction of the bodily fluid to the exterior of the capillary.

Figure 8:
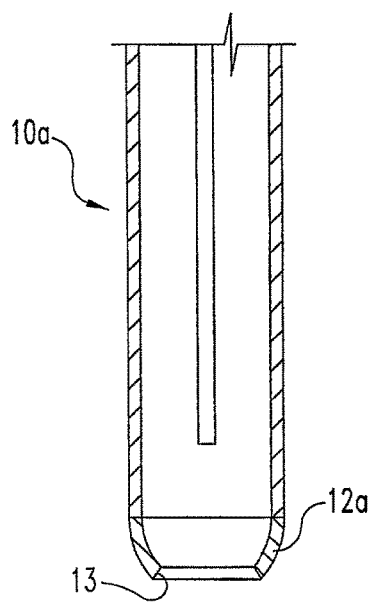
FIGS. 8-10 are partial, cross-sectional views showing alternate configurations of the expression member.
Figure 9:
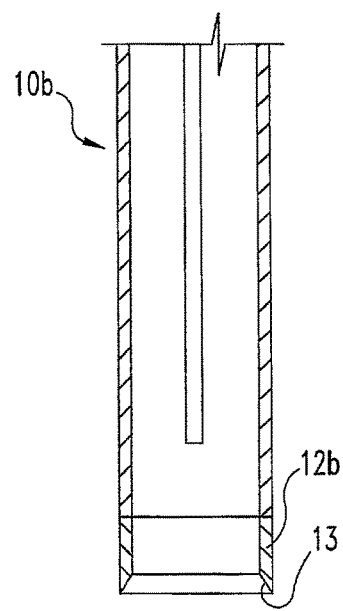
Figure 10:
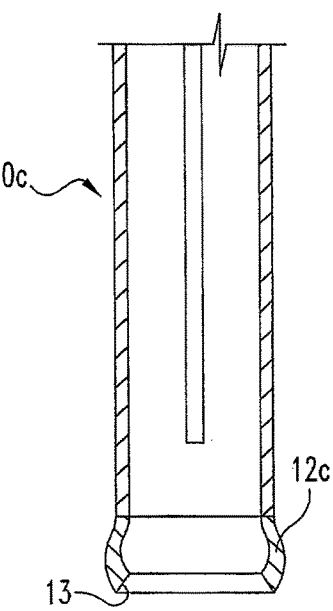
Figure 11:
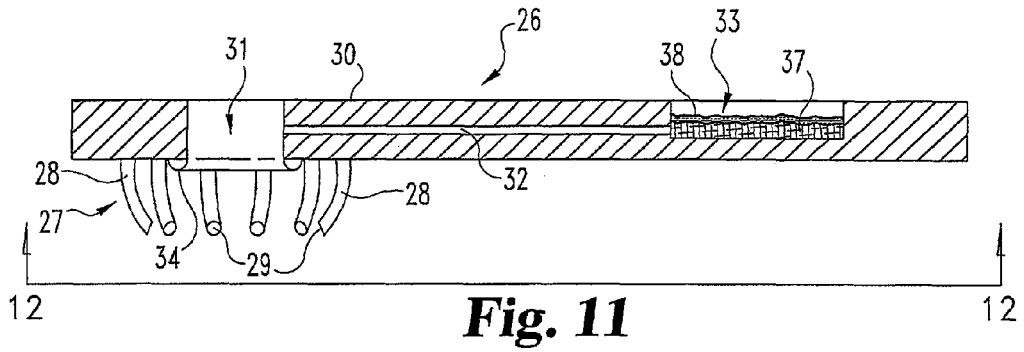
FIG. 11 is a side, cross-sectional view of a test strip including an expression system in accordance with an alternate embodiment of the present invention.

The constriction member may assume a variety of particular shapes and compositions. For example, referring to FIGS. 8-10, there are shown several expression devices 10a-10c having alternative configurations for the constriction member 12. As these drawings demonstrate, the shape of the constriction member may include such variations as rounded (12a), squared (12b) and bulged (12c) profiles. The skin-engaging surfaces 13 may be perpendicular with or angled to the adjacent portion of the constriction member, the longitudinal axis of the device 10, and/or the skin surface. The shapes and sizes are selected such that the deformation of the member provides a desired grasping and constriction of the skin.

The constriction member may be formed in a variety of manners. The member may be a single, unitary material. Alternatively, the member may be formed from several individual members that are separately attached to the housing or are joined together as an integral unit. The member may be uniform in composition, or it may be constructed of different materials, including materials having different physical properties, such as different durometers or other parameters that allow for tailoring the deformation characteristics of the member. For example, the flex or other deformation rate of different portions of the constriction member may be selected to control the rate and shape in which the member deforms, thereby controlling the manner in which the skin is constricted.

The constriction member is generally shown as having a diameter comparable to that of the housing. However, this should not be considered as limiting. Instead, the member may also be formed having a diameter greater or less than the diameter of the housing or other supporting structure. It is within the scope and intent of the present invention that the shape, size and other characteristics may be widely varied in order to provide a desired constricting of the skin to achieve the purposes set forth herein.

In an alternative embodiment, the constriction system utilizes several discrete members, rather than a single continuous member, which engage the skin and pinch it inwardly. Referring in particular to FIGS. 11-14, there is shown an embodiment of the constriction system in combination with alternative lancing, sampling and testing systems. In this version, the sampling system comprises a test strip 26 including a constricting system 27 attached to the underside thereof. The constricting system is shown as including several discrete, deformable elements 28, each element defining a surface 29 to engage the skin and move it inwardly to constrict the skin in the manner described with respect to the prior embodiments. This embodiment is shown in the drawings as including several arm-like structures, although various other shapes of the constricting elements are also suitable.

Figure 12:
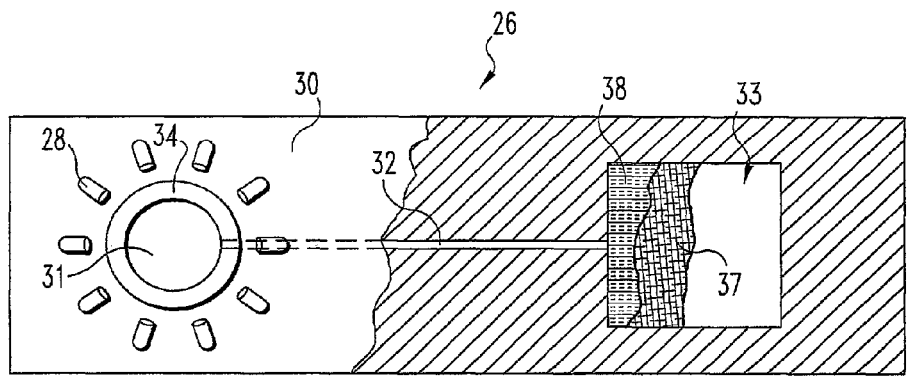
FIG. 12 is a bottom, plan view of the test strip of FIG. 11, partially in cross section.
Figure 13:
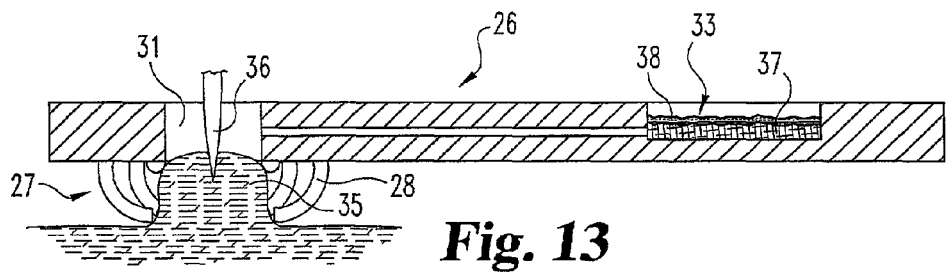
FIG. 13 is a side, cross-sectional view of the test strip of FIG. 11, showing the expression system in the constricting position.

In the use of a plurality of discrete elements, the positioning of such elements is variable. It is preferred that the elements are selected to be spaced apart and to generally surround the incision site. The elements are therefore preferably provided such that at least two elements are positioned to be on opposite sides of the incision site, but also any additional number of elements may be included. In a preferred embodiment, the elements include skin-engaging surfaces 29 positioned to fall within a circular pattern (FIG. 12). The elements preferably deform in a manner to move the skin-engaging surfaces in a radially-inward direction from the first positions to the second positions. In this embodiment, the elements are then preferably positioned to be diametrically-opposed, or equi-radially spaced about the incision site.

The strip 26 is preferably combined in an integrated unit which further includes components for the purposes of incising the skin and collecting the produced fluid sample. The test strip includes a body 30 defining an opening 31, a capillary passageway 32, and a test area 33. A sealing ring 34 is attached to or formed integrally with the underside of the body 30 in a position surrounding the opening 31 and interior of the deformable arms 28. The sealing ring may be constructed from any material that will suitably conform to and seal with the skin, including silicon, urethane, rubber, latex and various other natural and synthetic materials that are biocompatible. Alternatively, the sealing ring may be formed from a hard material such as plastics, metal, ceramic or other materials in order to provide a seal when pressed against the user's skin.

The use of the test strip system 26 proceeds as follows. The test strip 26 is pressed against the skin such that the arms 28 engage the skin and deform inwardly, thereby creating and retaining a bulged skin area 35. The skin is drawn upward and inward to an extent that it bears against the sealing ring 34, forming a fluid tight seal therewith. This assures that any fluid exiting the incision will be retained within the opening 31, rather than moving out under the test strip body. The sealing ring further functions to press against the skin, thereby providing an additional expression force, and pulling on the skin to open the incision when formed. Also, the contact of the skin with the sealing ring locates the skin at a controlled position to facilitate the formation of the incision at a desired depth and position.

A lancing device 36 is extended downwardly through opening 31 to lance the skin to the desired, controlled depth. The lancet is then withdrawn (FIG. 14) and bodily fluid 37 is allowed to form at the incision site. When the fluid accumulates to a sufficient extent, it contacts the entrance of the passageway 32 and is drawn into and through the passageway by capillary action. The fluid moves to the test area 33, such as by wicking into an absorbent material 37, and there contacts the test reagent 38 positioned on top of the wicking material.

Figure 14:
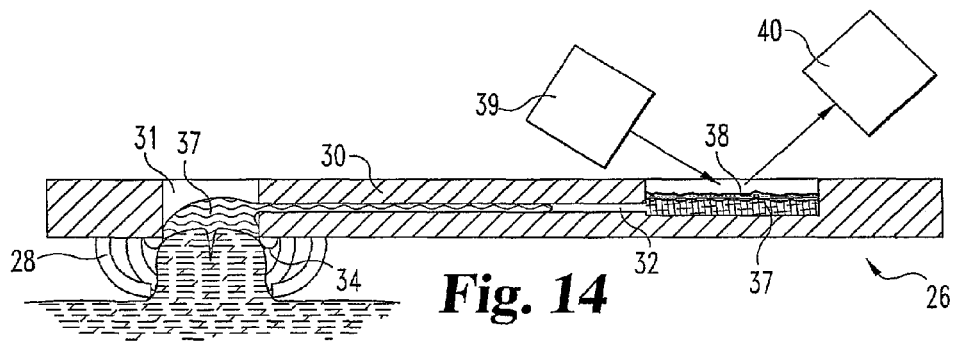
FIG. 14 is a side, cross-sectional view of the test strip of FIG. 11, showing the bodily fluid being acquired by the capillary passageway in the test strip.

The fluid is thereby presented in the test area and can be tested by conventional means, such as by reacting the fluid with the test reagent and analyzing the reaction product by optical or electrochemical means. For example, shown diagrammatically in FIG. 14 is a light source 39 for directing light against the test reagent, and a blood glucose meter 40 for receiving light reflected from the test reagent. In conventional fashion, the meter analyzes the reflected light to determine the result of the reaction between the bodily fluid and the test reagent. In this manner, a wide variety of analytes and properties of the fluid may be determined. Such test systems are well known in the art and therefore are not further described herein.

This embodiment provides another example of an integrated device which combines the expression system with incising, sampling and/or testing of the bodily fluid. This embodiment also demonstrates a device which would be suitable for the use of deformable expression elements which could be formed to flex, or to deform in a partially or fully non-reversible manner. A test strip of this type is preferably used once and then discarded, and it would therefore be suitable to provide expression elements that deform in a permanent manner. In use, the test strip is pressed against the skin to automatically deform the expression arms, thereby grasping and constricting the skin. Bodily fluid expressed from the incision is collected and tested, and the test strip is thereafter disposable.

In a similar manner, the constriction system may use rigid, movable, skin-engaging elements. For example, as shown in FIGS. 15-17, the constriction system may include a plurality of non-deforming arms 41 pivotally attached to the housing 42 by attachment to support blocks 43 with pins 44. For simplicity of explanation, two opposed arms 41 are shown in the figures. However, any larger number of separate arms may also be used, preferably spaced evenly about the incision site.

The arms function in the same manner as described with respect to the deforming members of the prior embodiments. The arms have a first, radially-outward position (FIG. 15) at which they initially contact the skin. The arms are pivotable about pins 44 to a second, radially-inward position (FIG. 16) in which the skin is pinched and bulges upwardly as previously described.

The arms may be constructed in various ways to provide the described functionality. The arms may be curved, angled or otherwise shaped to allow for movement from the outer position to the inner position to pinch the skin. The arms may be oriented to automatically pivot inward when pressed against the skin. Alternatively, the arms may be biased to the inward position by springs or other biasing means (not shown), which biasing may be released manually or automatically to urge the arms to the inner position. This movement occurs as the device is maintained in contact with the skin, and may occur automatically as the device is pressed against the skin. The arms may be constructed of any materials having suitable strength and rigidity, including various biocompatible plastics and metals.

This alternate embodiment is equally useful with the variety of additional components as described with respect to the previous embodiment. For example, the constriction members are useful as a stand-alone expression device, or in combination with various incising and/or sampling systems, optionally including testing systems. The expression system is shown in FIG. 16 in combination with an annular capillary lancet as described with respect to previous embodiments. In the use of this combination, the capillary 45 or other sampling device may have a recessed position (FIG. 15) displaced from the position for receiving fluid (FIG. 16). In that case, the capillary is moved downwardly toward the skin from the initial, displaced position to the fluid-receiving position to place the end opening of the capillary passageway at a location where it will contact the bodily fluid when it appears. The lancet 46 is extended beyond the capillary and incises the skin as previously described, and the resulting fluid contacts and enters the capillary passageway.

A further embodiment within the purview of the present invention is shown in FIGS. 18-20. The device 47 comprises a housing 48 having a deformable expression member 49 secured to the distal end. The expression member may be formed from a variety of materials as previously described, and may be attached by any suitable means, including gluing or otherwise fastening the material to the housing. The expression member 49 is shown as having a generally rounded shape, although alternative shapes may be used. The member may include several projections 50 or other structures designed to engage the skin as described hereafter.

The expression member 49 is configured to have two stable positions with the member either extended or inverted, shown particularly in FIGS. 19 and 20, respectively. The member in the extended position is located adjacent the skin 51 in the area intended for fluid sampling. The device is then pressed against the skin and the member 49 inverts (FIG. 20), and in the process the skin is engaged and drawn into the cavity thereby formed in the expression member. This drawing in of the skin is facilitated by the engagement of the projections 50 with the skin. The member 49 thereby operates, in the manner previously discussed, to retain bodily fluid within the area and to apply pressure to the skin to facilitate the expression of fluid from an incision formed therein.

Once the bi-stable, dynamic bevel member 49 has been inverted (FIG. 20), the skin is lanced and the bodily fluid expressed from the incision. For example, the device 47 includes an annular capillary lancet system 52 as described and shown with respect to FIGS. 2-7. The system includes a capillary tube 53 positioned within the housing 48 such that the end of the capillary will be proximate to the expression member 49 when such member is in the inverted position retaining the skin. The lancet 54 is extended beyond the end of the capillary tube and passes through a central opening 55 in the expression member to lance the skin. The lancet is then withdrawn and bodily fluid is expressed from the incision and through the opening 55. As the fluid sample grows it will make contact with the end of the capillary tube and will be drawn therein. Alternatively, the incision may be formed prior to applying the bi-stable member to the skin, but this is not preferred.

The opening 55 is sized to allow for the expression of the fluid from the incision. In one respect, the size of the opening is not critical, provided that it is large enough to permit the fluid to pass readily therethrough. In some instances, however, it may be desirable to provide an opening of a given, minimum dimension in order to further enhance the expression of the fluid. The opening may have any desired shape, but it is typically round and preferably has a minimum dimension of about 2 mm, and more preferably at least about 7 mm.

The outer surface of the constriction member 49 may be configured in a variety of ways to promote engagement of the skin. In a preferred embodiment, the member 49 includes outwardly-extending projections 50 that will contact and grasp the skin as the member inverts. The member may alternatively include other surface features to promote the engagement of the skin, including various surface projections or textures, or treatments such as coatings which stick to the skin.

The constriction devices of the present invention provide several advantages for the expression of a bodily fluid from an incision. As already described, the constriction of the skin maintains bodily fluid within the area of the incision site, and also applies a pressure to the skin that will tend to force fluid toward the incision. The constriction devices in certain embodiments also apply pressure to the skin in a manner which increases with the distance from the incision. For example, the drawing in of the skin by the bi-stable dynamic bevel will result in the skin being drawn the tightest in the area adjacent to the perimeter of the member 49, with less tension present toward the center. This provides a greater force at the perimeter to maintain the fluid therein, and to urge the fluid toward the center, and at the same time provides less tension toward the center in order to allow the fluid to move more freely toward and out of the incision. Correspondingly, the constriction devices in certain embodiments provide a pulling force at the center of the constricted space, thereby urging the incision open to facilitate the expression of bodily fluid from the incision.

The present invention also contemplates the use of members which are pressed against the skin, as distinguished from constricting the skin, to enhance the expression of bodily fluid from an incision.

In the embodiments of FIGS. 21-24, there are provided fluid expression devices, each of which includes a housing with a pressing element attached at the distal end thereof. The pressing element comprises a material having physical properties and a configuration to provide the desired application of force against the skin.

In one aspect of the invention, the element is designed to press against the skin in a manner to apply pressure in a predetermined pattern that urges the desired bodily fluid to move toward the incision site. In one approach, the element is configured to apply the greatest pressure at the outermost position, and to provide less pressure inwardly thereof. In a second approach, the element is configured to apply pressure initially at the outermost position, and to thereafter apply pressure at successively inward locations as the element is further urged against the skin. In addition, both approaches can be combined in a single design.

Referring to the drawings, there is shown an expression device 56 including a housing 57 and a deformable, pressing member 58. The pressing member 58 is depicted as comprising a series of segments 59 distributed radially about the housing. Each segment is generally wedge shaped with the taper extending in the direction of the centerline of the housing. In addition, ridges 60 and 61 extend upwardly from the wedge-shaped bodies.

Figure 22:
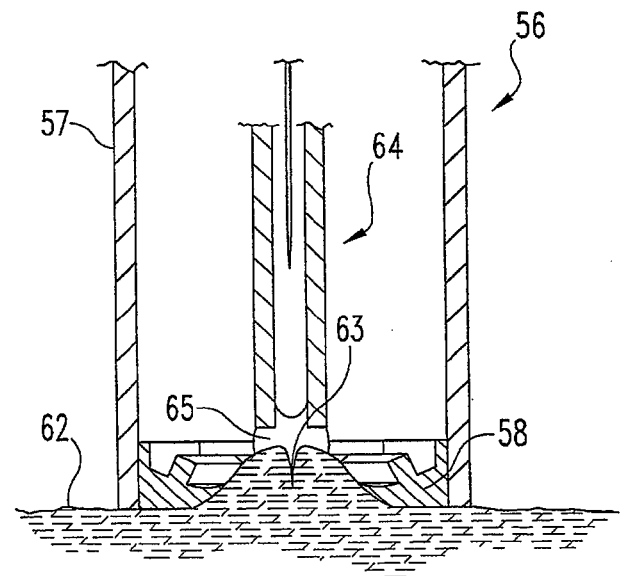
FIG. 22 is a side, cross-sectional view of the device of FIG. 21, showing the expression elements in the deformed condition.

The expression device 56 is used by pressing the device against the skin 62 at the desired sampling site. In this embodiment, the segments 59 are deformable, either by flexing, or in a partially or fully non-reversible manner. For purposes of illustration, the device is hereafter described with respect to flexible elements. As the device is pressed into the skin, the flexible segments 48 are forced upward, and spread apart slightly. The wedge shape of the segments causes the pressing members to provide greater resistance nearer the perimeter of the housing 57, and lesser resistance in the direction toward the center of the device. The ridges 60 and 61 further provide flexing characteristics of the segments, thereby varying the resistance to flexing afforded by such segments. The result is that the skin 64 extends upwardly into the open end of the housing, with the applied pressure against the skin being greatest at the radially-outermost positions, and lesser in the direction of the center of the housing (FIG. 22). This produces a pressure gradient in which the pressure on the skin decreases in the direction from the perimeter to the incision site. This urges bodily fluid along the gradient in the direction of the incision. An incision 63 is formed generally at the center of the pressing segments, such as by use of an annular capillary lancet system 64, as described with respect to previous embodiments. The produced fluid 65 contacts the capillary passageway and is drawn therein.

As previously described, another aspect of the present invention is the fact that the pressing elements will tend to open the incision by pulling the skin in the radially-outward direction. As the device is pressed into the skin, the greater pressure applied at the outer portions will more firmly engage the skin and will apply this radially-outward force to the skin. Therefore, a stretching force is imparted to the skin, which will cause the incision to pull apart. In addition, the skin-engaging surfaces 66 of the flexible members 59 may be configured to increase the friction with the skin in order to further produce this stretching force. For example, projections such as shown in FIG. 18, or other surface features, may be provided on the surfaces 66 to cause the members to further grasp the skin as the device is pressed into the skin.

It will be appreciated that the shape, size, material and other parameters for the pressing member can be varied in order to achieve the desired effects. For example, the pressing member 58 is shown as comprising several separate, but contiguous, members. Alternatively, the member 58 may be formed from several spaced-apart members, or may comprise a unitary, continuous member. While shown as having a wedge shape with upwardly extending ridges, the member may also have varying configurations with regard to cross-section, projections and the like. The pressing member may be formed from a single material or from a combination of materials, and a wide variety of materials may be used to obtain the desired physical characteristics. Such materials include, for example, various natural and synthetic materials, including polyvinyl chloride, silicon, urethane, and the like.

The pressing member may also be configured to first apply pressure at radially outer locations, followed by pressure application radially-inward thereof. This can be accomplished in a variety of ways. For example, the pressing member may be positioned such that the skin-engaging surface is inwardly and rearwardly angled such that contact with the skin first occurs at the radially outermost locations and moves progressively inwardly therefrom. Alternatively, the skin-engaging surface may be provided with projections which extend further in the radially-outermost locations.

Figure 23:
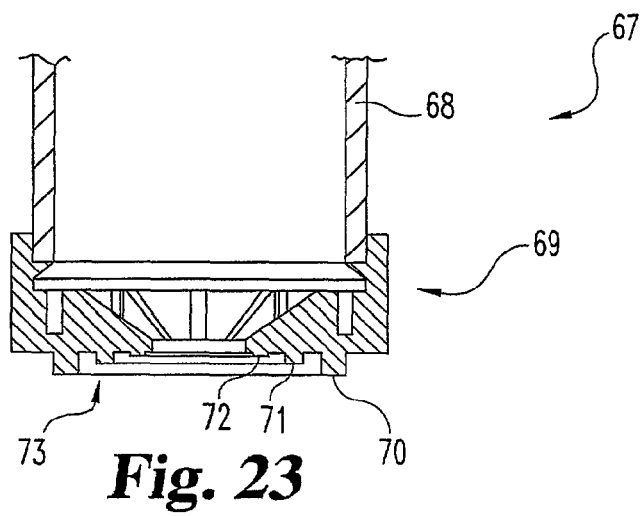
FIG. 23 is a side, cross-sectional view of an alternate embodiment of the expression system of FIG. 21.
Figure 24:
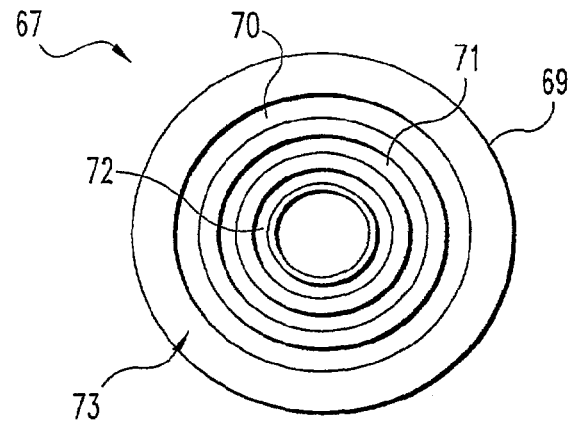
FIG. 24 is a distal end, elevational view of the expression system of FIG. 23.

Referring to FIGS. 23-24, there is shown another embodiment of an expression device including a deformable pressing member constructed in accordance with the present invention. The device 67 includes a housing 68 and a pressing member 69 attached thereto. This embodiment demonstrates the use of varying length projections 70-72 extending outwardly from the skin-engaging surface 73 of the pressing member 69. The outermost ring 70 extends the farthest and will therefore engage the skin first as the device is pressed against the skin. The second ring 71 will next engage the skin, followed by the third ring 72, as the device is moved further against the skin. In this manner, a force will first be applied by the outer ring 70, and this force will be the greatest applied against the skin as the device is advanced. The result is that the expression device 67 will apply compressive forces against the skin which move progressively inward, and which reduce in amount in the same, radially-inward direction. Each of these conditions will urge bodily fluid toward the centerline of the device, thereby promoting the expression of the fluid from a centered incision. It will be appreciated that this effect may be accomplished whether the pressing member is deformable, e.g., flexible, or not, although a flexible pressing member is preferred.

Figure 21:
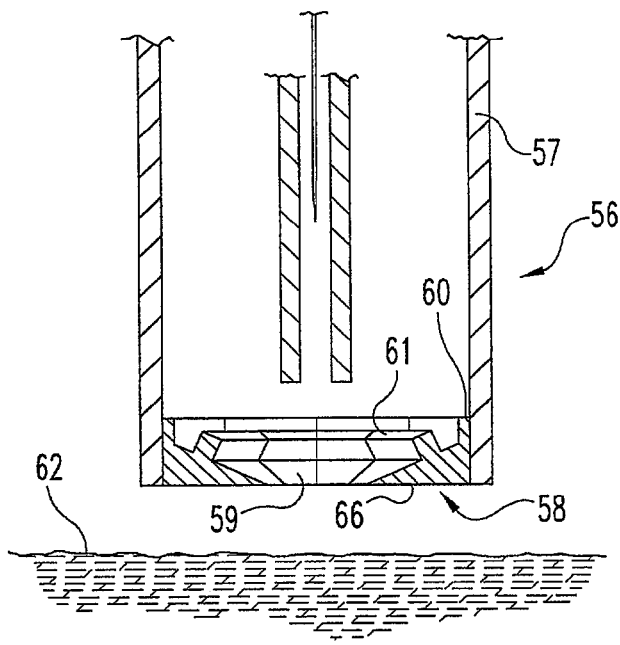
FIG. 21 is a side, cross-sectional view of an additional embodiment of an expression system according to the present invention.

The embodiments of FIGS. 21-24 further demonstrate that the pressing member may be mounted to the housings in various ways. In the embodiment of FIG. 21, for example, the pressing member is mounted within the supporting housing 56. The pressing member may alternatively be mounted at the end edge of the housing, on the exterior of the housing as shown in FIG. 23, or in any other manner that positions the skin in the desired location relative to the overall device, for example to enable lancing and/or sampling.

A variety of other expression systems utilizing members specially configured or operable to press the skin to express bodily fluid are also known in the art, and are useful in accordance with the present invention. In one embodiment, the expression device includes a fixed pressing surface, typically annular in shape and preferably including an internal aperture having a minimum diameter, such as 6 mm. In particular respects, the pressing surface includes a surface which tapers inwardly and rearwardly, providing a frusto-conical shape that bears against the skin. Examples of such fixed, pressing surfaces are described in U.S. Pat. Nos. 5,964,718 and 6,066,103. Alternatively, combination, rigid pressing members have also been disclosed in the art. For example, disclosed in U.S. Pat. Nos. 5,951,493, 6,071,250, and 6,319,210 are expression devices which include a first, outer pressing member and a second, inner pressing member. The pressing members are generally coaxial, and may be pressed against the skin either separately or at the same time. In one aspect, the members are pressed against the skin in a particular pattern, such as by first pressing the outer member against the skin and then pressing the inner member against the skin to urge the bodily fluid to move toward a central incision site. In another aspect, the members are pressed in an alternating pattern to knead the skin and form a peristaltic pumping of the fluid.

Other pressing systems have also been identified for urging bodily fluid toward an incision site. For example, in U.S. Pat. Nos. 5,951,493, 6,071,250, and 6,319,210 there are described expression systems that include a coil spring that is pressed against the skin. The use of rollers that press against the skin and are then moved radially inward to push fluid toward the center are described in U.S. Pat. Nos. 5,951,493 and 6,332,871.

The present invention further contemplates the combination of the foregoing expression systems. It will be apparent from the drawings that the expression systems are directly combinable to provide the advantages of the separate systems in a single device. For purposes of further illustration, exemplary combinations of the expression systems are provided hereafter. For example, referring to FIG. 25, there is shown a testing device 74 including a housing 75 and a combination expression system 76 secured thereto. The expression system includes a constriction member 77 shown in the inner, constricting position forming the bulged pinch of skin 78. In addition, a deformable pressing member 79 is mounted in the interior of the housing 75 and is positioned to also bear on the pinch of skin 78.

Figure 25:
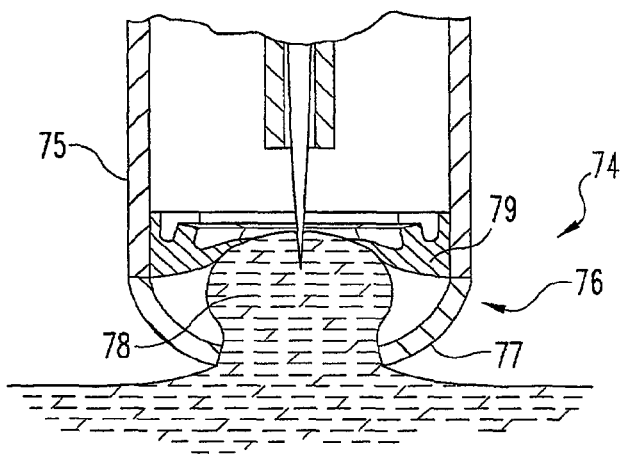
FIG. 25 is a partial, cross-sectional view of a fluid sampling device including a combined expression system in accordance with one embodiment of the present invention.
Figure 26:
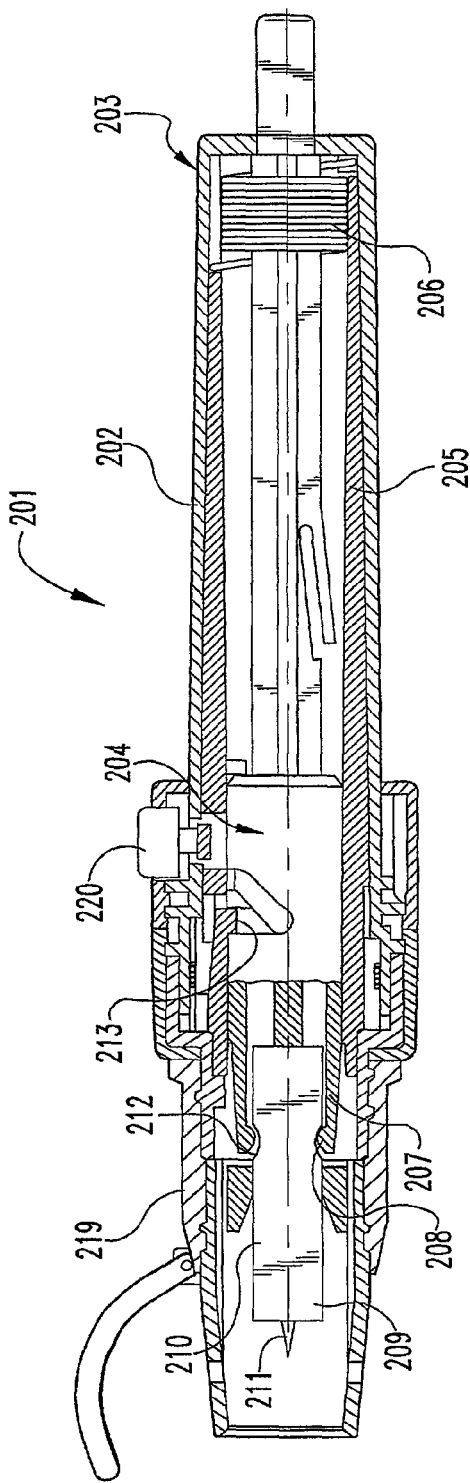
FIG. 26 is a side, cross-sectional view of a lancing device further incorporating an expression system of the present invention.
Figure 27:
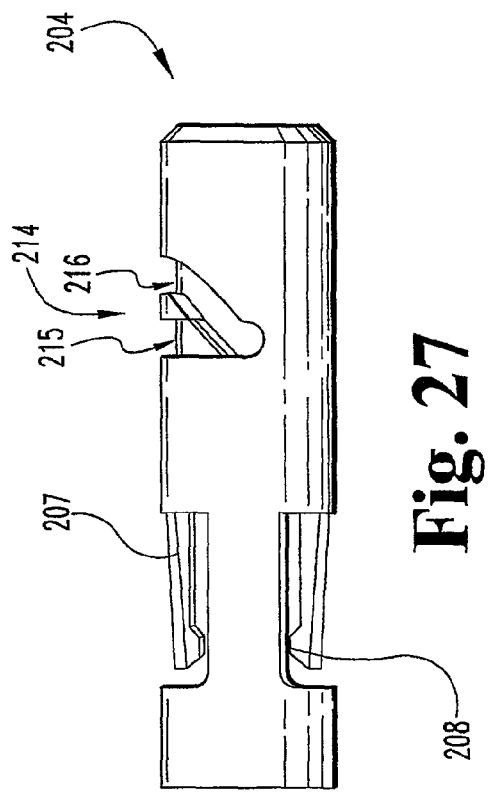
FIG. 27 is a side, elevational view of a lancet holder useful in the device of FIG. 26.

As this embodiment demonstrates, the combination of the different expression systems provides a device that achieves expression in ways, and to an extent, which may not be available from the individual systems. In one sense, the combination such as shown in FIG. 25 provides the constricting function of the constriction member 76, and the pressing function of the deformable pressing member 79. In addition, it will be noted that the combination causes each system to operate somewhat differently from what might occur separately. For example, the addition of the pressing system provides additional pressure for expressing fluid, and also provides additional forces to help pull and maintain the incision open after it has formed. On the other hand, the addition of the constricting member to the deformable pressing system helps to retain fluid in the area of the skin where the pressing member is bearing against the skin. The application of a pressing member alone is accomplished by pushing the member against the skin, which may exclude fluid that is not within the perimeter of the pressing member, and further may force some fluid out of the pressing area as the device is pressed against the skin. However, in accordance with the combined system, the pressing member does not bear against the skin until the skin has already been engaged by and pulled inward by the constricting system. The skin is actually pulled up against the pressing member. Therefore, the pressing member will not exclude or force out bodily fluid in the same manner that may otherwise occur without the constricting member, and the result is that additional fluid may be available at the incision site.

The following embodiments further demonstrate that the expression systems are readily adapted for use with various incising, sampling and/or testing devices. Referring in particular to FIGS. 26-29, a typical lancing device is shown except that it has been modified to include an exemplary expression system in accordance with the present invention. The basic lancing device, absent the expression system, is further described in U.S. Pat. No. Re 35,803, the disclosure of which is hereby incorporated by reference. Therefore, for illustrative purposes, only the major components of said device are shown in the drawings and described herein.

The lancing device 201 includes a housing 202 which contains a lancet drive mechanism 203 and a lancet holder 204. The drive mechanism includes a rotatable sleeve 205 and a spirally-wound, coiled spring 206 coupled between the housing and the rotatable sleeve. The lancet holder 204 is longitudinally slidable within the sleeve 205 and includes arms 207 with end lugs 208 that are receivable within recesses formed in a lancet component. The lancet component 209 includes a body 210 and a lancet tip 211. The lancet body defines a circumferential recess 212 which receives the end lugs 208 of the arms of the lancet holder 204. The lancet 209 is thereby longitudinally movable inside of the sleeve 205 in concert with the movement of the lancet holder 204.

The rotatable sleeve 205 includes a drive pin 213, and the lancet holder 204 defines a driver cam 214. The driver cam includes a first cam segment 215 to allow for cocking of the mechanism. The driver cam further includes a second, symmetrical, arcuate cam segment 216 to provide for projection and withdrawal of the lancet tip relative to the housing opening 217 formed in the pressing member 218 of the housing. An outer ring 219 connects with the rotatable sleeve 205 and upon rotation of the outer ring the sleeve is also rotated to tension the spring 206 as the drive pin 213 moves within the first cam segment 215. The rotatable sleeve automatically locks once in the fully tensioned position.

Upon pressing a lock release button 220, the sleeve rotates back to its original position. During this return rotation, the drive pin 213 moves within the second cam segment 216, causing the lancet holder and lancet initially to translate longitudinally of the sleeve 205 and housing 202 in a direction to drive the lancet tip to incise the skin. The lancet tip 211 is immediately thereafter withdrawn by operation of the second cam segment 216 of the lancet holder.

Figure 28:
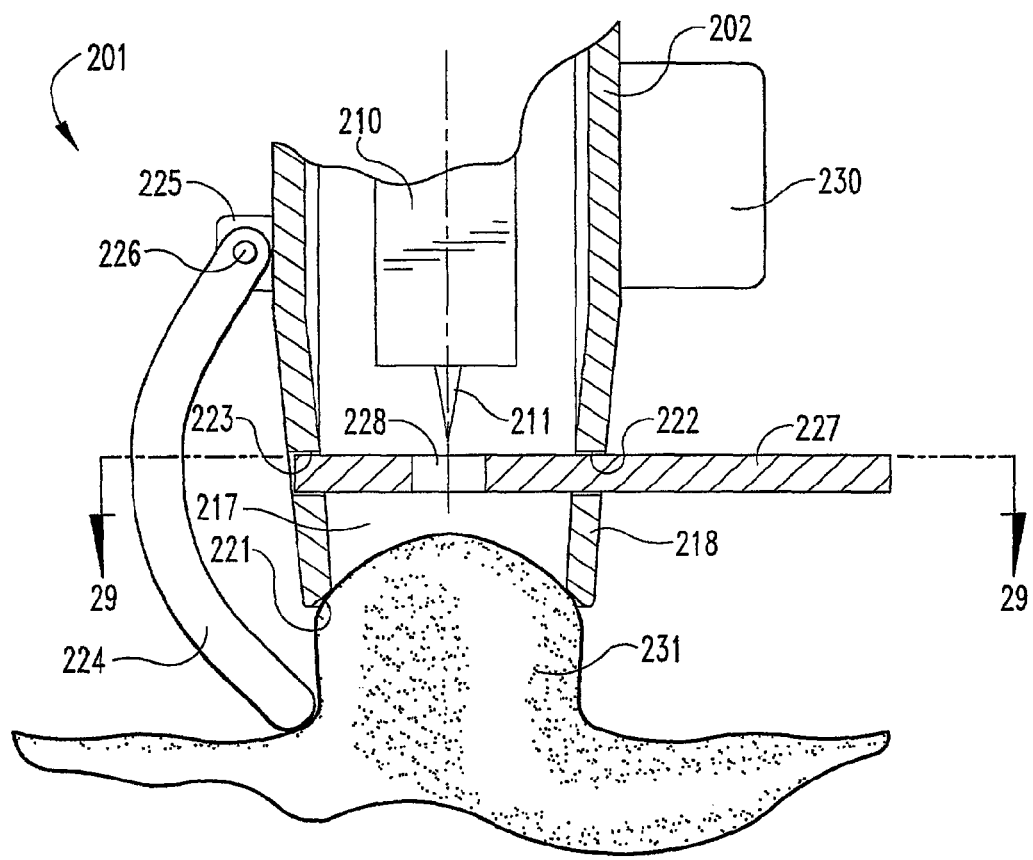
FIG. 28 is a partial, cross-sectional view of the skin-engaging portion of the device of FIG. 26, and further showing a test strip mounted therein.
Figure 29:
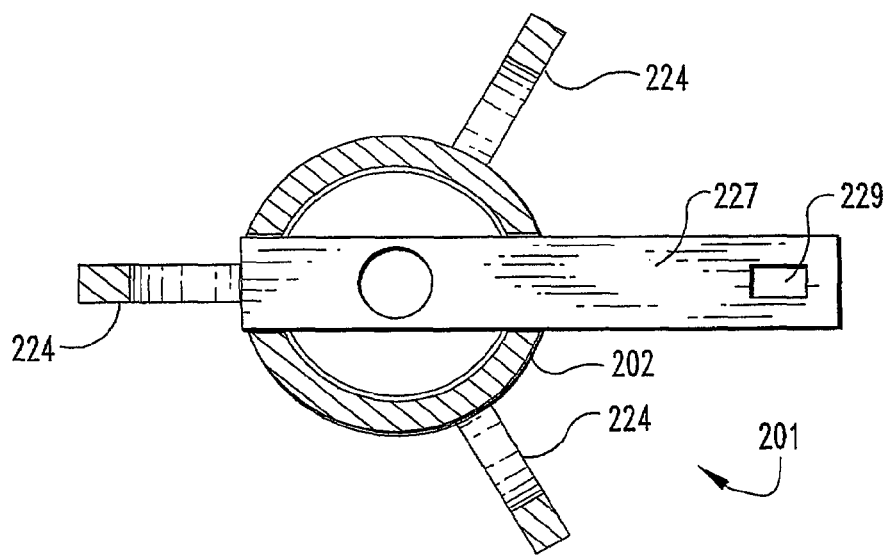
FIG. 29 is a cross-sectional view of the device of FIG. 26 taken along the line 26-26 and viewed in the direction of the arrows.

The pressing member extends to an annular surface 221 and defines slots 222 and 223 adjacent thereto. Three pivoting expression arms 224 are secured to the housing in equi-radially spaced positions by means of yokes 225 and pins 226. Each arm 224 has a first, spread position (FIG. 26), and is movable from this initial position to the second, constricting position (FIG. 28).

A test strip 227 is received within the slots 222-223 and includes an aperture 228 which is thereby positioned in line with the lancet 211. The test strip includes a capillary passageway (not shown) that extends from an inlet opening which communicates with the aperture 228 to a test region 229. The test region includes suitable reagent to interact with the bodily fluid which is received in the test region. An optical test device 230 is mounted to the housing and is positioned to evaluate the results of the reaction in the test region.

In accordance with the present invention, the integrated device 201 is operable as follows. The device is pressed against the skin and the arms 224 are manipulated from the open position to the constricting position (FIG. 28). The skin 231 is thereby drawn in to form a raised pinch of skin that bears against the annular surface 221. The lancet 211 is then advanced through the aperture 228 in the test strip and incises the skin. As a fluid droplet forms, it contacts the capillary passageway of the test strip 227 and is transported to the test region 229. The fluid then reacts with the reagent provided in the test region, and the results are read by the test device 230.

The foregoing description provides a representative sample of a lancing device useful in accordance with the present invention. It will be appreciated, however, that the particular lancing device and method are not limiting to the present invention, which finds utility with innumerable lancing systems. By way of further example, other representative lancing mechanisms include those shown in U.S. Pat. No. 4,924,879, issued to O'Brien on May 15, 1990; U.S. Pat. No. 5,879,311, issued to Duchon et al. on Mar. 9, 1999; U.S. Pat. No. 5,857,983, issued to Douglas et al. on Jan. 12, 1999; U.S. Pat. No. 6,015,392, issued to Douglas et al. on Jan. 18, 2000; U.S. Pat. No. 6,048,352, issued to Douglas et al. on Apr. 11, 2000; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 6,332,871, issued to Douglas et al. on Dec. 25, 2001; U.S. Pat. No. 5,964,718, issued to Duchon et al. on Oct. 12, 1999; U.S. Pat. No. 6,066,103, issued to Duchon et al. on May 23, 2000; and U.S. Pat. No. 6,086,545, issued to Roe et al. on Jul. 11, 2000.

Figure 30:
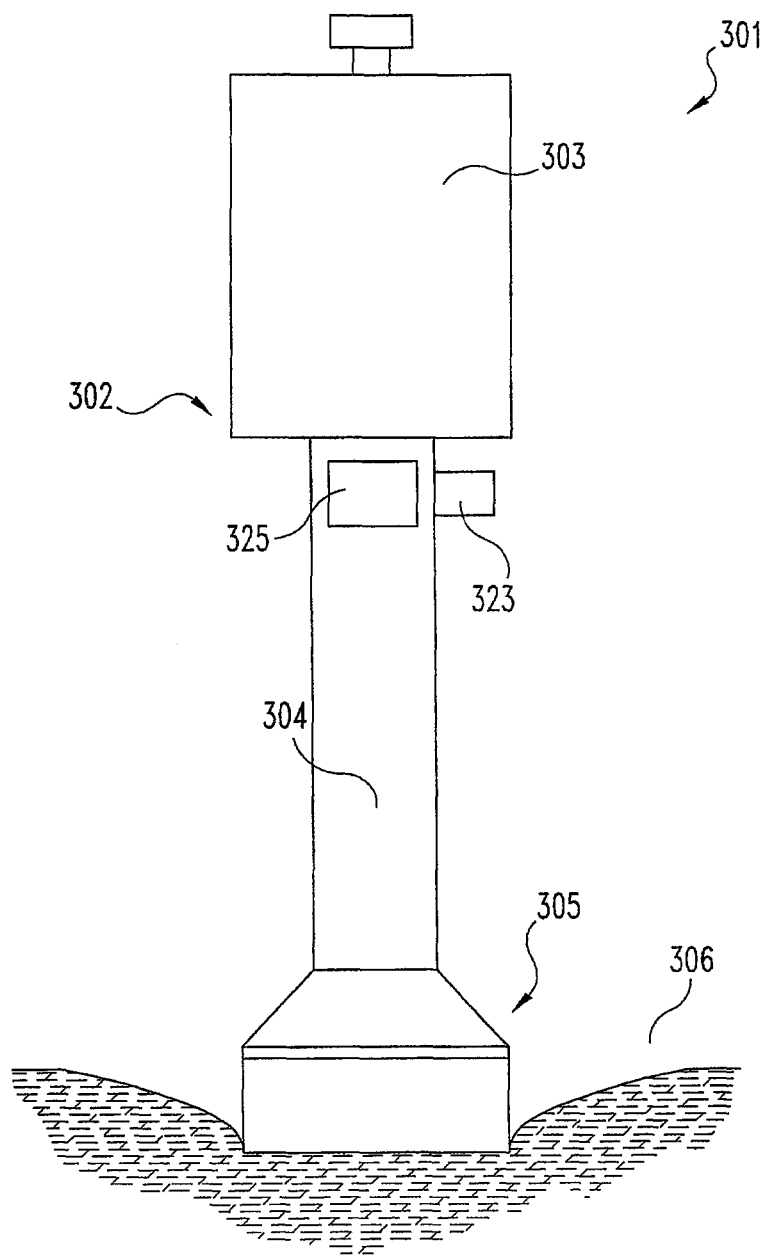
FIG. 30 is a side, elevational view of an alternate embodiment of an integrated fluid testing device according to an embodiment of the present invention.

An alternate, totally integrated fluid monitoring device is shown in FIG. 30. The integrated device 301 includes a housing 302 which includes or supports components operable to lance, express, sample and test bodily fluids. The housing includes a first member 303, a cylindrical extension member 304, and an expression system 305. The device 301 is shown in FIG. 30 as being contacted against the skin 306 in the position prior to expression of bodily fluid.

Figure 31:
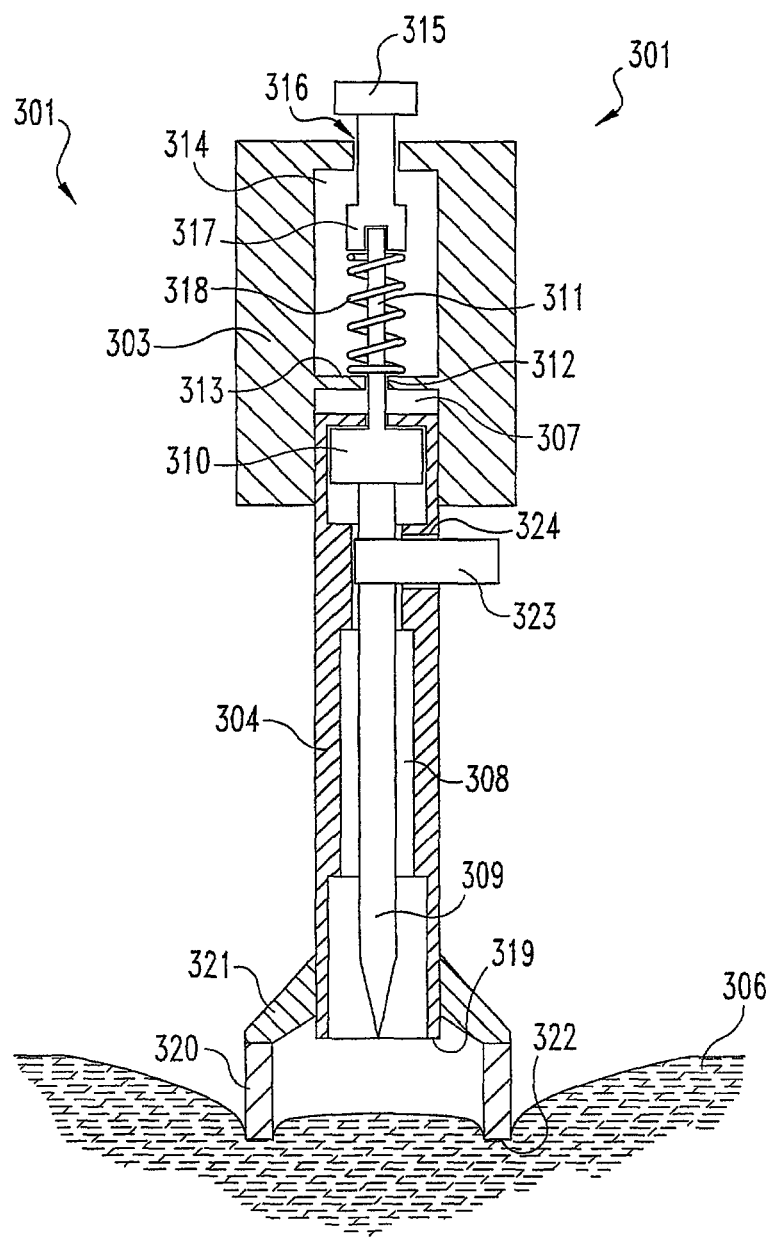
FIGS. 31 and 32 are partial, cross-sectional views of the fluid testing device of FIG. 30, showing in particular the expression of fluid from the skin and movement of the fluid up to the test area.

The components of the integrated device 301 are shown in detail beginning in FIG. 31. The cylindrical member 304 is mounted within a cavity 307 defined by the first member 303, and is secured therein, such as by a press fit or by gluing. The cylindrical member 304 defines an interior passageway 308, and a lancet 309 is received therein. The space between the lancet and the cylindrical member therefore defines an annular passageway, which is sized to provide a capillary attraction to the desired bodily fluid, as later described.

The lancet 309 is mounted to a lancet carrier 310 which includes an extension 311. The extension passes through an aperture 312 formed in an interior wall 313 of the member 302. The member 302 further defines a chamber 314 in which the extension 311 is received. A lancet button 315 is received through an aperture 316 in the member 302 and includes a mounting yoke 317 which is connected with the lancet carrier extension 311. A coil spring 318 is positioned around the extension 311 and is bears at one end on the yoke 317, and at the other end on the wall 313. In this manner, pressure applied against the button 315 will urge the lancet beyond the distal end 319 of the cylindrical member 304 for lancing the skin. Upon release of the downward pressure, the spring 318 will withdraw the lancet back into the cylindrical member 304, thereby removing the lancet from the incision formed in the skin.

Figure 32:
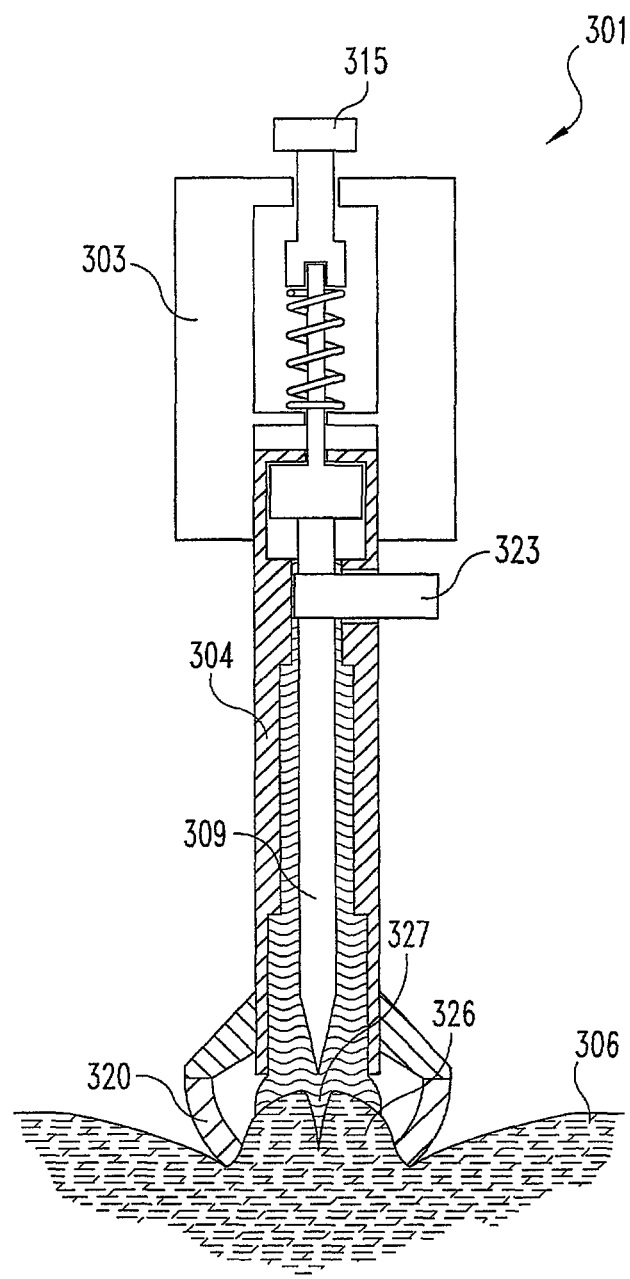

The device 301 further includes an expression system 305 attached to the cylindrical member 304. In particular, the expression system includes a cylindrical expressing member 320 secured to a support 321 which is in turn attached to or formed integrally with the cylindrical member 304. The expressing member 320 is deformable to facilitate the expression of fluid from an incision positioned interior of the member. The expressing member has an initial condition in which the skin-engaging surface 322 contacts the skin at a radially-outward position (FIG. 31). Upon further pressing the device 301 against the skin, the member 320 deforms inwardly, thereby grasping and moving the skin upward and inward to a constricted position (FIG. 32). This movement applies pressure against the skin to hold bodily fluid within the constricted area and to urge the fluid toward the center.

A test strip 323 is received through an aperture 324 in the wall of the cylindrical member 304. The test strip extends within the annular passageway between the lancet 309 and the interior of the cylindrical member 304, and therefore is in position to be contacted by fluid received in the passageway. A window 325 is located in the side of the cylindrical member 304 at a position to allow the test strip to be viewed from the exterior of the device. Therefore, the results of a reaction between the bodily fluid and the test strip can be observed through the window 325. Alternative test systems, including optical and electrochemical systems for example, are equally useful in accordance with the present invention.

The integrated device is operable to provide complete lancing, expressing, sampling and testing of a bodily fluid as follows. As shown in the drawings, the device 301 is initially positioned against the skin at the locating desired for fluid acquisition. The device is then pressed against the skin sufficiently to deform the expressing member 320, as shown in FIG. 32. This results in the creation of a raised pinch of skin 326. A force is then applied to the button 315 to move the lancet downwardly into the skin to form an incision 327. The force is immediately released from the button and the lancet retracts from the incision into the cylindrical member, as shown in FIG. 32. A droplet of bodily fluid will begin to form at the incision site, facilitated by the expressive forces applied to the skin by the expressing member 320.

As the droplet grows in size, it contacts the end opening of the passageway 308 and is drawn in by capillary action. The fluid sample continues to be drawn into the passageway until it contacts the test strip 323. The test strip is selected to provide a test of the desired constituent or property of the bodily fluid being sampled. The results are obtained by optical detection of the reaction through the window 325.

It will be appreciated from the foregoing descriptions that the several forms of expression comprising the present invention are useful independently of the presence or type of incising, sampling or testing systems. In certain embodiments, however, the expression mechanisms and methods are combined with incising, sampling and/or testing systems. It will be appreciated by those skilled in the art that the function of the expression system is achieved independent of the incising and sampling systems, and therefore is useful with a variety of such systems as are known in the art. However, the expression systems are advantageously combined with incising and sampling systems in a single, integrated device. Because the expression is achieved essentially independently of these other systems, the expression system is readily adapted as an additional component of such devices. It will similarly be appreciated that the integrated device may also combine testing means to test desired constituents or characteristics of the fluid sample that has been acquired. Further, this integrated operation is available for all of the expression systems described herein. For example, the expression systems are useful in combination with a wide range of incising, sampling and testing systems, including those herein described in the description of the prior art and elsewhere, and the disclosures of such patents are hereby incorporated by reference.

As shown in the drawings, such an integrated device preferably operates such that the device does not have to be repositioned at any time during the process of incising, expressing, and/or sampling. More specifically, the device preferably carries incising, expressing, sampling and testing systems to perform a complete, integrated monitoring of the bodily fluid. In accordance with this approach, the device is moved against the skin and is maintained in this position while the incision is formed, and also while the resulting fluid droplet develops and is carried into the sampling device. The fluid is then analyzed by the test system and the result of the analysis is provided to the user. All of these actions therefore may be accomplished by a single, integrated unit, providing a simple, quick and reliable method for acquiring and testing a bodily fluid.

Moreover, the combination of the various systems in a single unit assures that the separate systems will be properly coordinated in use. The timing for the formation of the constricted pinch of skin and the lancing of the skin can be controlled automatically, or by manual operation by the user. The positions of the incision site and of the sampling capillary tube are predetermined to optimize the acquisition of the fluid formed at the incision site. This reduces the potential for a user to fail to successfully collect the fluid that is produced.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for expressing and testing bodily fluid obtained from an incision in the skin, the method comprising:
    attaching a first disposable test strip to a lancing device with a lancet, the first disposable test strip including a test strip integrally formed with a first constricting member, a first fluid passageway, and a first test area;
    bulging the skin toward an opening to the first fluid passageway and expressing bodily fluid from the incision by pressing skin-engaging surfaces of the first constricting member against the skin and moving the skin-engaging surfaces toward one another, wherein the opening to the first fluid passageway is located on the surface of the first test strip adjacent the first constricting member;

lancing the bulged skin with the lancet to create an incision;

drawing the bodily fluid by capillary action from the skin through the opening and along the first fluid passageway to the first test area, the first test area being in fluid communication with the first fluid passageway;

testing the bodily fluid in the first test area;

removing the first test strip from the lancing device and disposing of the first test strip; and attaching a second disposable test strip to the lancing device, the second disposable test strip including a second constricting member, a second fluid passageway, and a second test area.

2. The method of claim 1, wherein the opening on the surface of the first test strip defines an aperture extending through the test strip, and wherein said lancing includes the lancet extending through the aperture in the test strip, each constricting member including a plurality of elements surrounding the opening, each element including a skin-engaging surface, wherein said moving includes moving the plurality of elements with the skin-engaging surfaces radially inward from outer to inner positions.

3. The method of claim 1, wherein each constricting member includes a plurality of flexible elements surrounding said opening, each flexible element including a skin-engaging surface, wherein said moving includes flexing the plurality of flexible elements with the skin-engaging surfaces moving radially inward from outer to inner positions.

4. The method of claim 1, further comprising orienting the lancet approximately orthogonal to the skin surface at the incision site before said bulging and during said lancing.

5. A method for expressing and testing bodily fluid obtained from an incision in the skin, the method comprising:

attaching a first disposable test strip to a lancing device with a lancet, the first disposable test strip including a test strip integrally formed with a first constricting member, a first capillary tube, and a first test area;

bulging the skin toward an opening to the first capillary tube and expressing bodily fluid from the incision by pressing skin-engaging surfaces of the first constricting member against the skin;

moving the skin-engaging surfaces from initial, outer positions to constricting, inner positions, wherein the opening to the first capillary tube is located on the surface of the first test strip adjacent the first constricting member;

lancing the bulged skin with the lancet to create an incision;

drawing the bodily fluid by capillary action from the skin through the opening and along the first capillary tube to the first test area, the first test area being in fluid communication with the first capillary tube;

testing the bodily fluid in the first test area;

removing the first test strip from the lancing device and disposing of the first test strip; and attaching a second disposable test strip to the lancing device, the second disposable test strip including a second constricting member, a second capillary tube, and a second test area.

6. The method of claim 5, further comprising:

flexing the first constricting member by pressing the skin-engaging surfaces of the first constricting member against the skin.

7. The method of claim 6, wherein each constricting member includes a plurality of deformable elements surrounding said opening, each deformable element including a skin-engaging surface, wherein said moving includes moving the plurality of skin-engaging surfaces radially inward from the outer to the inner positions.

8. The method of claim 5, wherein the opening to the first capillary tube defines an aperture extending through the test strip, and wherein said lancing includes extending the lancet through the aperture in the test strip, each constricting member including a plurality of elements surrounding the opening, each element including a skin-engaging surface, wherein said moving includes moving the plurality of elements with the skin-engaging surfaces radially inward from outer to inner positions.

9. The method of claim 5 further comprising:

orienting the lancet perpendicular to the skin surface at the incision site during said bulging.

10. The method of claim 9, further comprising:

orienting the lancet perpendicular to the skin surface at the incision site during said lancing.

11. An apparatus for expressing and testing bodily fluid obtained from an incision in the skin, the apparatus comprising:

a lancing device for forming an incision in the skin; and an integrated test strip with a bottom surface; said test strip attached to said lancing device during sampling with said test strip bottom surface facing the skin, said integrated test strip including:

a constricting member for constricting the skin, said constricting member integrally formed with said test strip and extending from said test strip bottom surface to at least two skin-engaging surfaces, a fluid passageway for collecting bodily fluid, said fluid passageway integrally formed with said test strip and including an opening on the surface of said test strip adjacent said constricting member, wherein said skin-engaging surfaces move closer together and draw the skin inward toward said opening as said at least two skin-engaging surfaces contact and are pressed against the skin, a test area including a test reagent for testing bodily fluid, said test area integrally formed with said test strip and in fluid communication with said fluid passageway; and wherein said integrated test strip, said constricting member, said fluid passageway and said test area are removable from said lancing device as a single unit and are disposable as a single unit.

12. The apparatus of claim 11, wherein said opening defines an aperture sized to receive a lancet extending through the test strip, said opening extending through said test strip, and wherein said test strip being attached to said lancing device to align said test strip aperture and said lancet with said lancet extending downwardly through said opening to lance the skin, each constricting member including a plurality of elements surrounding the opening, each element including a skin-engaging surface, wherein said moving includes moving the plurality of elements with the skin-engaging surfaces radially inward from outer to inner positions.

13. The apparatus of claim 11, wherein said constricting member includes a plurality of deformable elements, each deformable element including a skin-engaging surface.

14. The apparatus of claim 13, wherein said plurality of deformable elements surrounds said opening.

15. The apparatus of claim 13, wherein said deformable elements are elongated, arm-like structures.

16. The apparatus of claim 11, wherein said test strip includes a sealing ring surrounding said opening, wherein said at least two skin-engaging surfaces draw the skin inward to contact said sealing ring and form a fluid tight seal between the skin and the sealing ring.

17. The apparatus of claim 11, wherein said passageway includes a capillary channel that draws fluid from said passageway opening by capillary action.

18. The apparatus of claim 11, wherein said test strip is flat and narrow and said constricting member extends from the bottom surface of said flat and narrow test strip that faces the skin.

* * * * *